(12) United States Patent
Kashino

(10) Patent No.: US 10,639,263 B2
(45) Date of Patent: May 5, 2020

(54) METHOD FOR ADJUSTING HARDNESS OF STICK-SHAPED BASE MATERIAL COMPRISING LIPID PEPTIDE COMPOUND

(71) Applicant: NISSAN CHEMICAL INDUSTRIES, LTD., Tokyo (JP)

(72) Inventor: Tsubasa Kashino, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 244 days.

(21) Appl. No.: 15/739,957

(22) PCT Filed: Jun. 14, 2016

(86) PCT No.: PCT/JP2016/067693
§ 371 (c)(1),
(2) Date: Dec. 26, 2017

(87) PCT Pub. No.: WO2016/208460
PCT Pub. Date: Dec. 29, 2016

(65) Prior Publication Data
US 2018/0353414 A1    Dec. 13, 2018

(30) Foreign Application Priority Data

Jun. 24, 2015 (JP) .................... 2015-127112
Jun. 30, 2015 (JP) .................... 2015-131883

(51) Int. Cl.
| | | |
|---|---|---|
| *A61K 8/64* | (2006.01) | |
| *A61K 8/39* | (2006.01) | |
| *A61K 8/02* | (2006.01) | |
| *A61K 8/04* | (2006.01) | |
| *A61Q 19/00* | (2006.01) | |
| *A61K 8/43* | (2006.01) | |

(52) U.S. Cl.
CPC .............. *A61K 8/64* (2013.01); *A61K 8/0229* (2013.01); *A61K 8/042* (2013.01); *A61K 8/39* (2013.01); *A61K 8/43* (2013.01); *A61Q 19/00* (2013.01)

(58) Field of Classification Search
CPC .......... A61K 8/64; A61K 8/39; A61K 8/0229; A61K 8/042; A61K 8/43; A61Q 19/00
See application file for complete search history.

(56) References Cited

FOREIGN PATENT DOCUMENTS

| | | |
|---|---|---|
| JP | H3-279319 A | 12/1991 |
| JP | 2000-511159 A | 8/2000 |
| JP | 2002-516818 A | 6/2002 |
| WO | 2011/052613 A1 | 5/2011 |
| WO | 2012/133787 A1 | 10/2012 |
| WO | 2014/054702 A1 | 4/2014 |
| WO | 2015/099074 A1 | 7/2015 |

OTHER PUBLICATIONS

Aug. 16, 2016 Written Opinion issued in International Patent Application No. PCT/JP2016/067693.
Aug. 16, 2016 International Search Report issued in International Patent Application No. PCT/JP2016/067693.

*Primary Examiner* — Juliet C Switzer
*Assistant Examiner* — Genevieve S Alley
(74) *Attorney, Agent, or Firm* — Oliff PLC

(57) ABSTRACT

A method for adjusting hardness of a stick-shaped base material including a lipid peptide compound. A method for adjusting hardness of a gelled solid base material for skin external application including a surfactant, water, and lipid peptide compound including compounds of formulae (1) or similar,

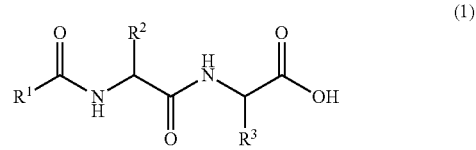

(1)

wherein $R^1$ is a $C_{9\text{-}23}$ aliphatic group, $R^2$ is a hydrogen atom or similar, and $R^3$ is a —$(CH_2)n$-X group, n is a number from 1 to 4, and X is amino group, the method including adding a pH adjuster to a solution in which the material is dissolved, or a solution including a surfactant, water, and lipid peptide compound including at least one of compounds of formulae (1) to (3) or pharmaceutically usable salts thereof, to adjust the pH of the solution to a weak acidic to neutral range, causing gelation of the solution to form a solid base material for skin external application.

5 Claims, 3 Drawing Sheets

METHOD FOR ADJUSTING HARDNESS OF STICK-SHAPED BASE MATERIAL COMPRISING LIPID PEPTIDE COMPOUND

TECHNICAL FIELD

The present invention relates to a method for adjusting hardness of a stick-shaped base material comprising a lipid peptide compound.

BACKGROUND ART

Aqueous solid compositions give a highly refreshing feeling at the time of application to skin and the like and give a less sticky feeling and a smoother and drier feeling after use than oleaginous solid compositions, and therefore, various goods containing aqueous solid compositions for cosmetics and the like have been proposed and put on the market.

As aqueous solid compositions, an oil-in-water type solid cosmetic for makeup containing water, fatty acid soap, oil, and powder (Patent Document 1), and a stick-shaped aqueous cosmetic containing an alkyl and/or alkenyl oligo glycoside, an oleaginous substance, and a nonionic emulsifier (Patent Document 2) have been conventionally proposed.

Furthermore, examples of aqueous solid compositions include aqueous gel compositions. As additives for obtaining the aqueous gels, various compounds, such as a polymer gelator and a low molecular weight gelator, have been proposed. In recent years, for example, a low molecular weight lipid peptide gelator that has a high level of living body safety and is expected to be developed to, for example, a biomedical material has been proposed.

PRIOR ART DOCUMENTS

Patent Documents

Patent Document 1: Japanese Patent Application Publication No. H3-279319 (JP 3-279319 A)
Patent Document 2: Japanese Patent Application Publication No. 2002-516818 (JP 2002-516818 T)

SUMMARY OF THE INVENTION

Problem to be Solved by the Invention

An aqueous gel obtained using the above-mentioned low molecular weight lipid peptide gelator has a relatively low breaking strength, and therefore, for applications requiring a considerable strength, such as application to a stick-shaped solid base material for skin external application, there has been desired a further improvement in the breaking strength of the aqueous gel, in particular, an increase in the breaking strength of the aqueous gel to a desired level, preferably with a simple technique.

In view of the above-mentioned situations, it is an object of the present invention to provide a method for increasing the breaking strength of the aqueous gel with a simple means, that is, a method for adjusting, to a desired level, the hardness of, for example, a stick-shaped solid base material for skin external application that contains a lipid peptide compound.

Means for Solving the Problem

As a result of intensive studies in order to solve the problem, the inventors of the present invention have found that, when the pH of a hydrogel formed of a surfactant, water, and a lipid peptide compound (gelator) including a low molecular weight lipid peptide or a pharmaceutically usable salt thereof is adjusted to a weak acidic to neutral range, the breaking strength of the hydrogel can be increased to a desired level, and furthermore, the pH adjustment allows the hardness of a solid base material for skin external application formed of the hydrogel to be maintained at a level suitable to the above-mentioned target applications, and the inventors have completed the present invention.

Specifically, the present invention relates to, as a first aspect, a method for adjusting the hardness of a gelled solid base material for skin external application, the solid base material including a surfactant, water, and a lipid peptide compound including at least one of compounds of formulae (1) to (3) below or pharmaceutically usable salts of the compounds, the method characterized by comprising:
adding a pH adjuster to a solution in which the solid base material for skin external application is dissolved, or a solution including a surfactant, water, and a lipid peptide compound including at least one of compounds of formulae (1) to (3) below or pharmaceutically usable salts of the compounds, to adjust the pH of the solution to a weak acidic to neutral range; and subsequently, causing gelation of the solution to form a solid base material for skin external application

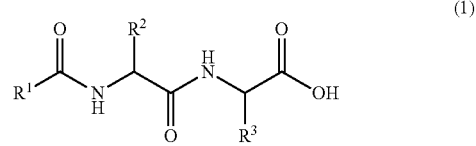

(1)

(wherein $R^1$ is a $C_{9-23}$ aliphatic group; $R^2$ is a hydrogen atom, or a $C_{1-4}$ alkyl group that optionally has a $C_1$ or $C_2$ branched chain; and $R^3$ is a —$(CH_2)_n$—X group, n is a number from 1 to 4, and X is amino group, guanidino group, —$CONH_2$ group, or a 5-membered or 6-membered ring group that optionally has 1 to 3 nitrogen atoms, or a condensed heterocycle group composed of the 5-membered ring and the 6-membered ring)

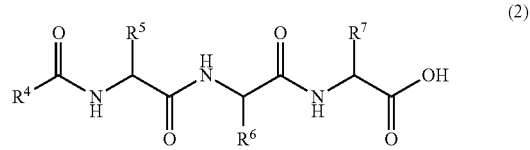

(2)

(wherein $R^4$ is a $C_{9-23}$ aliphatic group; $R^5$ to $R^7$ are each independently a hydrogen atom, a $C_{1-4}$ alkyl group that optionally has a $C_1$ or $C_2$ branched chain, or a —$(CH_2)_n$—X group, n is a number from 1 to 4, and X is amino group, guanidino group, —$CONH_2$ group, or a 5-membered or 6-membered ring group that optionally has 1 to 3 nitrogen atoms, or a condensed heterocycle group composed of the 5-membered ring and the 6-membered ring)

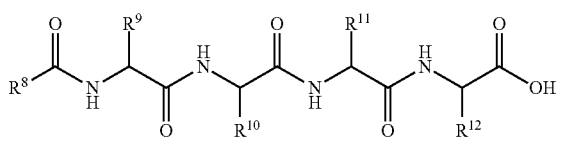

(3)

(wherein $R^8$ is a $C_{9-23}$ aliphatic group; $R^9$ to $R^{12}$ are each independently a hydrogen atom, a $C_{1-4}$ alkyl group that optionally has a $C_1$ or $C_2$ branched chain, or a —$(CH_2)_n$—X group, n is a number from 1 to 4, and X is amino group, guanidino group, —$CONH_2$ group, or a 5-membered or 6-membered ring group that optionally has 1 to 3 nitrogen atoms, or a condensed heterocycle group composed of the 5-membered ring and the 6-membered ring).

The present invention relates to, as a second aspect, the method according to the first aspect, in which the solution adjusted to be in the weak acidic to neutral range has a pH of 3.0 to 7.5.

The present invention relates to, as a third aspect, the method according to the first aspect or the second aspect, in which the pH adjuster is acetic acid, hydrochloric acid, sulfuric acid, sodium hydroxide, potassium hydroxide, or aqueous ammonia.

The present invention relates to, as a fourth aspect, the method according to any one of the first aspect to the third aspect, in which the solid base material for skin external application is used for cosmetics or pharmaceuticals.

The present invention relates to, as a fifth aspect, the method according to any one of the first aspect to the fourth aspect, in which the solid base material for skin external application is stick-shaped.

Effects of the Invention

The present invention enables the breaking strength of a hydrogel formed of a surfactant, water, and a gelator to be adjusted using a simple means, and in particular, the invention is suitable to achieve a hydrogel breaking strength required for applications of a stick-shaped solid base material for skin external application that is formed from the hydrogel.

Furthermore, according to the present invention, even in the case of a solid base material for skin external application that has been already formed from the hydrogel, by dissolving the solid base material for skin external application in a solution and adjusting the pH of the solution, the hardness of an original solid base material for skin external application can be adjusted (changed). Hence, according to the present invention, the hardness of a solid base material for skin external application that is formed from a hydrogel can be adjusted (changed) any number of times.

MODES FOR CARRYING OUT THE INVENTION

Figure 1:
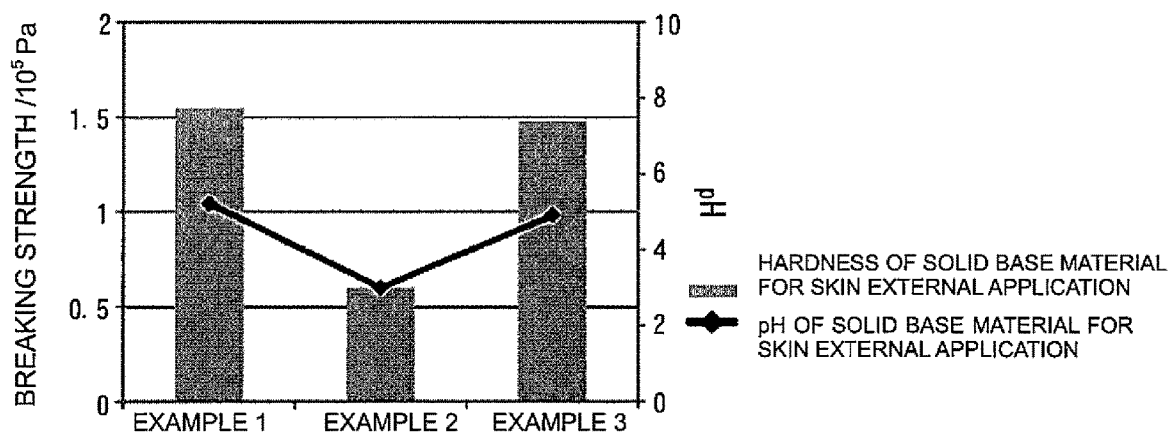
FIG. 1 is a graph showing the measurement results of the breaking strength of solid base materials for skin external application in Examples 1 to 3.

The present invention provides a method capable of adjusting the hardness of a hydrogel formed of a surfactant, water, and a gelator to a desired level, and in particular, the method is suitable to achieve a hydrogel breaking strength required for applications of a stick-shaped solid base material for skin external application that is formed from the hydrogel.

Furthermore, a solid base material for skin external application that has a hardness adjusted by the method according to the present invention can be used for various applications. Among various applications, the solid base material is particularly suitable for cosmetic and pharmaceutical applications.

In the present specification, the hardness of a solid base material for skin external application can be expressed by, for example, breaking strength measured using a breaking strength measurement apparatus. For example, using YAMADEN RHEONER II CREEP METER RE2-33005B (manufactured by Yamaden Co., Ltd.), the breaking strength of a solid base material for skin external application is measured until the break thereof under the conditions of a measurement speed: 0.5 mm/second, a measurement distortion factor: 20%, a storing pitch: 0.10 second, and a jig: 30349-3.

In terms of breaking strength measured using the above-mentioned breaking strength measurement apparatus, a breaking strength required as a stick-shaped base material is, for example, $0.4 \times 10^5$ Pa to $8.0 \times 10^5$ Pa, preferably $1.0 \times 10^5$ Pa to $7.0 \times 10^5$ Pa, more preferably $1.0 \times 10^5$ Pa to $6.0 \times 10^5$ Pa. Note that, in the present invention, a stick-shaped base material refers to a bar-shaped base material that has a strength enough to maintain the shape of a bar and enough to be applicable to skin (in other words, enough to maintain the shape when applied).

[Method for Adjusting the Hardness of Solid Base Material for Skin External Application]

A method for adjusting the hardness of a solid base material for skin external application according to the present invention includes a pH adjustment step and a step of forming a solid base material for skin external application.

<pH Adjustment Step>

The pH adjustment step is a step of adjusting the pH of a solution to a weak acidic to neutral range by adding a pH adjuster thereto, in which the solution is a solution containing a gelled solid base material for skin external application dissolved therein that includes a surfactant, water, and a lipid peptide compound including at least one of compounds of formulae (1) to (3) below or pharmaceutically usable salts thereof; or a solution including a surfactant, water, and a lipid peptide compound including at least one of compounds of formulae (1) to (3) below or pharmaceutically usable salts thereof.

The above-mentioned solid base material for skin external application is formed by gelation of a solution including a surfactant, water, and a lipid peptide compound including at least one of compounds of formulae (1) to (3) below or pharmaceutically usable salts thereof. Hence, in the present specification, the pH of the solid base material for skin external application is substantially the same as the pH of the solution including a surfactant, water, and a lipid peptide compound including at least one of compounds of formulae (1) to (3) below or pharmaceutically usable salts thereof.

Furthermore, in the present specification, also the pH of a solid base material for skin external application that is formed by gelation of a solution containing the above-mentioned solid base material for skin external application dissolved therein is substantially the same as the pH of a solution containing a gelled solid base material for skin external application dissolved therein that includes a surfactant, water, and a lipid peptide compound including at least one of compounds of formulae (1) to (3) below or pharmaceutically usable salts thereof.

The method of adding a pH adjuster to the above-mentioned solution is not limited to a particular method, and examples of the method include known methods, such as a method of adding a pH adjuster to the above-mentioned solution while measuring the pH of the solution, a method of measuring the pH of the above-mentioned solution to determine a pH adjuster amount required for adjusting the pH of the solution to a weak acidic to neutral range and subsequently adding the necessary amount of a pH adjuster, and a method of separately preparing a solution in which a pH adjuster is dissolved and adding the solution to the above-mentioned solution, or a method in which these methods are employed in combination.

Furthermore, a pH adjuster or a solution in which a pH adjuster is dissolved may be added all at once (one-time addition), or may be divided into small portions and added (dividing addition).

In the method according to the present invention, for example, when the pH of the above-mentioned solution becomes acidic by adding an acid as a pH adjuster, an alkali may be added to the solution to adjust the pH of the solution to a weak acidic to neutral range. When the pH of the above-mentioned solution becomes basic by adding an alkali as a pH adjuster, an acid may be added to the solution to adjust the pH of the solution to a weak acidic to neutral range.

The pH adjuster used at the above-mentioned pH adjustment step is not limited to a particular one as long as the adjuster is capable of adjusting the pH of the above-mentioned solution, and examples of the pH adjuster include acids and alkalis. Examples of such pH adjuster include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, sodium hydroxide, potassium hydroxide, aqueous ammonia, guanidine carbonate, and ammonium carbonate. Among them, acetic acid, hydrochloric acid, sulfuric acid, sodium hydroxide, potassium hydroxide, and aqueous ammonia are preferably employed.

Note that the pH adjuster used at the pH adjustment step according to the present invention is at least one of the above-mentioned pH adjusters, and these pH adjusters may be used alone or two or more of them may be used in combination.

The addition amount of the pH adjuster is not limited to a particular amount, and is only required to be enough to adjust the pH value of the above-mentioned solution to a weak acidic to neutral range. Such addition amount differs depending on the kinds of a surfactant, water, and a lipid peptide compound, and furthermore other ingredients that are contained in the above-mentioned solution, and the amounts of these ingredients blended, and thus the addition amount is appropriately selected so that the pH value is in the above-mentioned range.

The pH of the above-mentioned pH-adjusted solution is in a weak acidic to neutral range, specifically in a range of pH 3.0 to 7.5, preferably in a range of pH 3.5 to 7.5, more preferably in a range of pH 4.0 to 7.0. This is because, when the pH is less than 3.0 or more than 7.5, sometimes the solid base material for skin external application does not have a sufficient breaking strength required as a solid base material.

Note that, in the present specification, when a pH is in a neutral range, the pH is not limited to 7.0, but may be 6.5 to 7.5, for example.

The method of measuring the pH of the above-mentioned solution under pH adjustment or the pH of the above-mentioned pH-adjusted solution is not limited to a particular method, and is only required to be capable of performing pH measurement. Examples of the method include known methods, such as a measurement method using pH test paper and a measurement method using a pH meter (for example, Twin pH B-212, manufactured by HORIBA, Ltd.).

<Step of Formation of Solid Base Material for Skin External Application>

The formation step is a step of causing gelation of a solution having a pH adjusted to a weak acidic to neutral range through the above-mentioned pH adjustment step to form a solid base material for skin external application.

The method of gelation of the solution having a pH adjusted to a weak acidic to neutral range is not limited to a particular method, and is only required to cause gelation of the solution. Examples of the method include known methods, such as a method of cooling the solution, a method of concentrating the solution, and a method of adding the solution to a solvent such as water, and heating and cooling the resultant mixture.

Note that, in the case where the hardness of an obtained solid base material for skin external application differs from a target hardness, the hardness of the solid base material for skin external application can be adjusted (changed) to the target hardness by preparing a solution in which the solid base material for skin external application is dissolved in water or other solvents and adjusting the pH through the above-mentioned pH adjustment step.

[Solid Base Material for Skin External Application]

Hereinafter, a solid base material for skin external application having a hardness adjusted by the method according to the present invention will be described.

The solid base material for skin external application contains a surfactant, water, and a lipid peptide compound including at least one of compounds of formulae (1) to (3) below or pharmaceutically usable salts thereof.

<Lipid Peptide Compound>

As the lipid peptide compound to be contained in the above-mentioned solid base material for skin external application, compounds (lipid peptides) of formulae (1) to (3) below or pharmaceutically usable salts thereof (low molecular weight compounds having a lipid moiety serving as a hydrophobic moiety and a peptide moiety serving as a hydrophilic moiety) may be used.

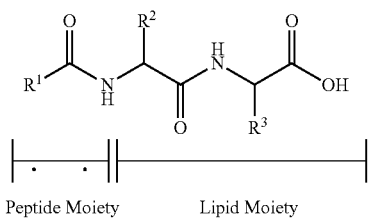

In formula (1), $R^1$ is a $C_{9-23}$ aliphatic group, preferably a linear aliphatic group having a carbon atom number of 11 to 23, in which the linear aliphatic group may have 0 to 2 unsaturated bonds.

Specific examples of the lipid moiety (acyl group) composed of $R^1$ and a carbonyl group adjacent thereto include lauroyl group, dodecylcarbonyl group, myristoyl group, tetradecylcarbonyl group, palmitoyl group, margaroyl group, oleoyl group, elaidoyl group, linoleoyl group, stearoyl group, vaccenoyl group, octadecylcarbonyl group, arachidoyl group, eicosylcarbonyl group, behenoyl group, elkanoyl group, docosylcarbonyl group, lignoceroyl group, and nervonoyl group, and particularly preferred examples thereof include lauroyl group, myristoyl group, palmitoyl group, margaroyl group, stearoyl group, oleoyl group, elaidoyl group, and behenoyl group.

In formula (1), $R^2$ included in the peptide moiety is a hydrogen atom, or a $C_{1-4}$ alkyl group that may have a $C_1$ or $C_2$ branched chain.

The $C_{1-4}$ alkyl group that may have a $C_1$ or $C_2$ branched chain refers to an alkyl group that has a $C_{1-4}$ main chain and may have a $C_1$ or $C_2$ branched chain. Specific examples of the $C_{1-4}$ alkyl group include methyl group, ethyl group, n-propyl group, i-propyl group, n-butyl group, i-butyl group, sec-butyl group, and tert-butyl group.

$R^2$ is preferably a hydrogen atom, or a $C_{1-3}$ alkyl group that may have a $C_1$ branched chain, and is more preferably a hydrogen atom.

The $C_{1-3}$ alkyl group that may have a $C_1$ branched chain refers to an alkyl group that has a $C_{1-3}$ main chain and may have a $C_1$ branched chain. Specific examples of the $C_{1-3}$ alkyl group include methyl group, ethyl group, n-propyl group, i-propyl group, i-butyl group, and sec-butyl group, and preferably methyl group, i-propyl group, i-butyl group, and sec-butyl group.

In formula (1), $R^3$ is a $-(CH_2)_n-X$ group. In the $-(CH_2)_n-X$ group, n is a number from 1 to 4; and X is amino group, guanidino group, $-CONH_2$ group, or a 5-membered or 6-membered ring group that may have 1 to 3 nitrogen atoms or a condensed heterocyclic group composed of the 5-membered ring and the 6-membered ring.

In the $-(CH_2)_n-X$ group serving as $R^3$, X is preferably amino group, guanidino group, carbamoyl group ($-CONH_2$ group), pyrrole group, imidazole group, pyrazole group, or indole group, and more preferably imidazole group. Furthermore, in the $(CH_2)_n-X$ group, n is preferably 1 or 2, more preferably 1.

Accordingly, the $-(CH_2)_n-X$ group is preferably aminomethyl group, 2-aminoethyl group, 3-aminopropyl group, 4-aminobutyl group, carbamoylmethyl group, 2-carbamoylethyl group, 3-carbamoylbutyl group, 2-guanidinoethyl group, 3-guanidinobutyl group, pyrrolemethyl group, 4-imidazolemethyl group, pyrazolemethyl group, or 3-indolemethyl group, more preferably 4-aminobutyl group, carbamoylmethyl group, 2-carbamoylethyl group, 3-guanidinobutyl group, 4-imidazolemethyl group, or 3-indolemethyl group, and still more preferably 4-imidazolemethyl group.

Particularly preferred examples of the lipid peptide compound of formula (1) include the following compounds each formed of a lipid moiety and a peptide moiety (amino acid assembly moiety), where amino acid abbreviations used here are alanine (Ala), asparagine (Asn), glutamine (Gln), glycine (Gly), histidine (His), isoleucine (Ile), leucine (Leu), lysine (Lys), tryptophan (Trp), and valine (Val): lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, lauroyl-Ala-Lys; myristoyl-Gly-His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Tip, myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, palmitoyl-Ala-Lys; and stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, stearoyl-Ala-Lys.

The most preferred lipid peptide compounds are lauroyl-Gly-His, lauroyl-Ala-His; myristoyl-Gly-His, myristoyl-Ala-His; palmitoyl-Gly-His, palmitoyl-Ala-His; and stearoyl-Gly-His, stearoyl-Ala-His.

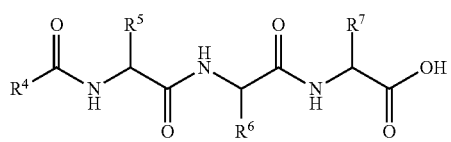

In formula (2), $R^4$ is a $C_{9-23}$ aliphatic group, and preferred specific examples of $R^4$ include the same groups as defined as the above-mentioned $R^1$.

In formula (2), $R^5$ to $R^7$ are each independently a hydrogen atom, a $C_1$ alkyl group that may have a $C_1$ or $C_2$ branched chain, or a $-(CH_2)_n-X$ group, and preferably at least one of $R^5$ to $R^7$ is a $-(CH_2)_n-X$ group. n is a number from 1 to 4, and X is amino group, guanidino group, $-CONH_2$ group, or a 5-membered or 6-membered ring group that may have 1 to 3 nitrogen atoms or a condensed heterocyclic group composed of the 5-membered ring and the 6-membered ring. Here, preferred specific examples of $R^5$ to $R^7$ include the same groups as defined as the above-mentioned $R^2$ and $R^3$.

Preferred examples of the lipid peptide compound of formula (2) include the following compounds each formed of a lipid moiety and a peptide moiety (amino acid assembly moiety): lauroyl-Gly-Gly-His, myristoyl-Gly-Gly-His, myristoyl-Gly-Gly-Gln, myristoyl-Gly-Gly-Asn, myristoyl-Gly-Gly-Trp, myristoyl-Gly-Gly-Lys, myristoyl-Gly-Ala-His, myristoyl-Gly-Ala-Gln, myristoyl-Gly-Ala-Asn, myristoyl-Gly-Ala-Trp, myristoyl-Gly-Ala-Lys, myristoyl-Ala-Gly-His, myristoyl-Ala-Gly-Gln, myristoyl-Ala-Gly-Asn, myristoyl-Ala-Gly-Trp, myristoyl-Ala-Gly-Lys, myristoyl-Gly-His-Gly, myristoyl-His-Gly-Gly, palmitoyl-Gly-Gly-His, palmitoyl-Gly-Gly-Gln, palmitoyl-Gly-Gly-Asn, palmitoyl-Gly-Gly-Trp, palmitoyl-Gly-Gly-Lys, palmitoyl-Gly-Ala-His, palmitoyl-Gly-Ala-Gln, palmitoyl-Gly-Ala-Asn, palmitoyl-Gly-Ala-Trp, palmitoyl-Gly-Ala-Lys, palmitoyl-Ala-Gly-His, palmitoyl-Ala-Gly-Gln, palmitoyl-Ala- Gly-Asn, palmitoyl-Ala-Gly-Trp, palmitoyl-Ala-Gly-Lys, palmitoyl-Gly-His-Gly, palmitoyl-His-Gly-Gly, and stearoyl-Gly-Gly-His.

Among them, the most preferred compounds are lauroyl-Gly-Gly-His, myristoyl-Gly-Gly-His, palmitoyl-Gly-Gly-His, palmitoyl-Gly-His-Gly, palmitoyl-His-Gly-Gly, and stearoyl-Gly-Gly-His.

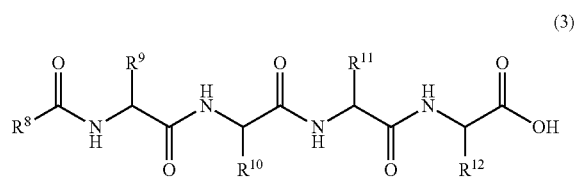

(3)

In formula (3), $R^8$ is a $C_{9-23}$ aliphatic group, and preferred specific examples of $R^8$ include the same groups as defined as the above-mentioned $R^1$.

In formula (3), $R^9$ to $R^{12}$ are each independently a hydrogen atom, a $C_{1-4}$ alkyl group that may have a $C_1$ or $C_2$ branched chain, or a —$(CH_2)_n$—X group, and preferably at least one of $R^9$ to $R^{12}$ is a —$(CH_2)_n$—X group. n is a number from 1 to 4, and X is amino group, guanidino group, —$CONH_2$ group, or a 5-membered or 6-membered ring group that may have 1 to 3 nitrogen atoms or a condensed heterocyclic group composed of the 5-membered ring and the 6-membered ring. Here, preferred specific examples of $R^9$ to $R^{12}$ include the same groups as defined as the above-mentioned $R^2$ and $R^3$.

Accordingly, particularly preferred examples of the lipid peptide compound of formula (3) include lauroyl-Gly-Gly-Gly-His, myristoyl-Gly-Gly-Gly-His, palmitoyl-His-Gly-Gly-Gly, and stearoyl-Gly-Gly-Gly-His.

In the present invention, the amount of the lipid peptide compound contained is, for example, 1% by mass to 20% by mass, preferably 1% by mass to 10% by mass, and more preferably 4% by mass to 5% by mass with respect to the total mass of an obtained solid base material for skin external application.

Note that the lipid peptide compound used in the solid base material for skin external application comprises at least one of compounds (lipid peptide) of formulae (1) to (3) above or pharmaceutically usable salts thereof, and as a hydrogelator, these compounds may be used alone or two or more of them may be used in combination.

<Surfactant>

As a surfactant used in the above-mentioned solid base material for skin external application, there may be preferably used a compound having a hydrophilic moiety having a betaine structure and a hydrophobic moiety in a molecule (hereinafter, also referred to as a betaine compound), an ethylene glycol alkyl ether, a polyglycerol fatty acid ester, or a polyoxyethylene polyoxypropylene alkyl ether.

As the above-mentioned betaine compound, there may be preferably used a betaine compound known as an amphoteric surfactant, for example, N-alkyl-N,N-dimethylamino acid betaines, such as lauryl dimethylaminoacetic acid betaine (lauryl betaine); fatty acid amido alkyl-N,N-dimethylamino acid betaines, such as cocamide propyl betaine and lauramide propyl betaine; imidazoline betaines, such as sodium cocoamphoacetate and sodium lauroamphoacetate; alkyl sulfobetaines, such as lauryl hydroxysulfobetaine and alkyl dimethyltaurines; betaine sulfates, such as alkyl dimethylaminoethanol sulfates; and betaine phosphates, such as alkyl dimethylaminoethanol phosphates may be used to serve as an amphoteric surfactant.

Furthermore, examples of the betaine compound include glycerophospholipids, such as phosphatidylcholine, phosphatidylethanolamine, phosphatidylserine, phosphatidylinositol, phosphatidylglycerol, diphosphatidylglycerol (cardiolipin), and phosphatidic acid; lysoglycerophospholipids, such as lysophosphatidylcholine (lysolecihin), lysophosphatidylethanolamine, lysophosphatidylserine, lysophosphatidylinositol, lysophosphatidylglycerol, and lysophosphatidic acid; sphingophospholipids, such as sphingomyelin; and hydrogenated derivatives of these phospholipids. These phospholipids may be animal- or plant-derived phospholipids, such as soybeans and egg yolks, or may be chemically or enzymatically synthesized phospholipids.

Among the above-mentioned betaine compounds, preferred examples of the betaine compound include lauryl dimethylaminoacetic acid betaine, lauramidopropyl betaine, lauryl hydroxysulfobetaine, stearyl betaine, lysophosphatidylcholine (lysolecihin), lysophosphatidylethanolamine, lysophosphatidylserine, lysophosphatidylinositol, lysophosphatidylglycerol, and lysophosphatidic acid, and more preferred examples thereof include lysophosphatidylcholine (lysolecihin).

Examples of the above-mentioned ethylene glycol alkyl ether include polyoxyethylene alkyl ethers, polyoxyethylene lauryl ethers, polyoxyethylene palmitoyl ethers, and polyoxyethylene stearylethers. Furthermore, a commercially available ethylene glycol alkyl ether may be used, and examples of such commercial products include, out of EMULGEN (registered trademark) series and EMANON (registered trademark) series manufactured by Kao Corporation, EMULGEN 102KG, EMULGEN 103, EMULGEN 104P, EMULGEN 105, EMULGEN 106, EMULGEN 108, EMULGEN 109P, EMULGEN 120, EMULGEN 123P, EMULGEN 130K, EMULGEN 147, EMULGEN 150, EMULGEN 210P, EMULGEN 220, EMULGEN 306P, EMULGEN 320P, EMULGEN 350, EMULGEN 404, EMULGEN 408, EMULGEN 409PV, EMULGEN 420, EMULGEN 430, EMULGEN 705, EMULGEN 707, EMULGEN 709, EMULGEN 1108, EMULGEN 1118S-70, EMULGEN 1135S-70, EMULGEN 11505-60, EMULGEN 4085, EMULGEN 2020G-HA, EMULGEN 2025G, EMANON 1112, EMANON 3199V, EMANON 3299V, EMANON 3299RV, and EMANON 4110. More preferred examples thereof include EMULGEN 103, EMULGEN 104P, EMULGEN 105, EMULGEN 106, EMULGEN 108, EMULGEN 109P, EMULGEN 210P, EMULGEN 306P, EMULGEN 320P, EMULGEN 404, EMULGEN 408, EMULGEN 409PV, EMULGEN 420, EMULGEN 705, EMULGEN 707, EMULGEN 709, EMULGEN 1108, EMULGEN 20200-HA, EMANON 1112, and EMANON 4110, each manufactured by Kao Corporation. Still more preferred examples of the commercial products include EMULGEN 104P, EMULGEN 105, EMULGEN 106, EMULGEN 108, EMULGEN 210P, EMULGEN 306P, EMULGEN 408, EMULGEN 409PV, EMULGEN 705, EMULGEN 707, EMULGEN 709, EMULGEN 1108, EMULGEN 20200-HA, EMANON 1112, and EMANON 4110, each manufactured by Kao Corporation. Besides these, also from NIKKOL (registered trademark) series manufactured by Nikko Chemicals Co., Ltd., the commercial product may be suitably selected. Examples of the suitably-selected NIKKOL series product include NIKKOL BT-5, NIKKOL BT-7, NIKKOL BT-9, and NIKKOL BT-12.

Examples of the above-mentioned polyglycerol fatty acid esters include glycerol fatty acid partial esters, such as glyceryl stearate, glyceryl isostearate, glyceryl palmitate, glyceryl myristate, glyceryl oleate, glyceryl cocoate, glycerol mono-cottonseed oil fatty acid esters, glycerol monoerucate, glycerol sesquioleate, glycerol α, α'-oleate pyroglutamate, and glycerol monostearate malate; polyglyceryl-2 stearates, polyglyceryl-3 stearates, polyglyceryl-4 stearates, polyglyceryl-5 stearates, polyglyceryl-6 stearates, polyglyceryl-8 stearates, polyglyceryl-10 stearates, polyglyceryl-6 distearates, polyglyceryl-10 distearates, polyglyceryl-2 tristearates, polyglyceryl-10 decastearates, polyglyceryl-2 isostearates, polyglyceryl-3 isostearates, polyglyceryl-4 isostearates, polyglyceryl-5 isostearates, polyglyceryl-6 isostearates, polyglyceryl-8 isostearates, polyglyceryl-10 isostearates, polyglyceryl-2 diisostearates (diglyceryl diisostearate), polyglyceryl-3 diisostearates, polyglyceryl-10 diisostearates, polyglyceryl-2 triisostearates, polyglyceryl-2 tetraisostearates, polyglycetyl-10 decaisostearates, polyglyceryl-2 oleates, polyglyceryl-3 oleates, polyglyceryl-4 oleates, polyglyceryl-5 oleates, polyglyceryl-6 oleates, polyglyceryl-8 oleates, polyglyceryl-10 oleates, polyglyceryl-6 dioleates, polyglyceryl-2 trioleates, and polyglyceryl-10 decaoleates.

Examples of the polyoxyethylene polyoxypropylene alkyl ether include EMULGEN (registered trademark) LS-106, EMULGEN LS-110, EMULGEN LS-114, and EMULGEN MS-110, each manufactured by Kao Corporation; and NIKKOL (registered trademark) PBC-31, NIKKOL PBC-33, NIKKOL PBC-34, NIKKOL PBC-41, NIKKOL PBC-44, NIKKOL PBN-4612, NIKKOL PBN-4620, and NIKKOL PBN-4630, each manufactured by Nikko Chemicals Co., Ltd. More preferred examples of polyoxyethylene polyoxypropylene alkyl ethers include EMULGEN LS-106, EMULGEN LS-110, EMULGEN LS-114, and EMULGEN MS-110. Still more preferred examples of the polyoxyethylene polyoxypropylene alkyl ethers include EMULGEN LS-106, EMULGEN LS-110, and EMULGEN MS-110.

As the above-mentioned surfactant, a surfactant having an HLB (Hydrophile-Lipophile Balance) value of 8 to 20 may be preferably used. A surfactant having an HLB value of 8 to 14 may be more preferably used.

Examples of such a surfactant include sorbitan isostearate, steareth-8, beheneth-10, laureth-5, ceteth-7, oleth-8, PEG-8 glyceryl isostearate, choleth-10, PEG-10BG isostearate, PEG-30 glyceryl triisostearate, PEG-30 glyceryl triisostearate, PEG-30 glyceryl trioleate, PEG-30 trimethylolpropane triisostearate, PEG-30 hydrogenated castor oil laurate, PEG-30 hydrogenated castor oil PCA isostearate, octyldodeceth-10, PEG-12 dilaurate, sorbeth-40 tetraoleate, polyglyceryl-10 diisostearates, PEG-20 glyceryl diisostearate, PEG-8 isostearate, PEG-10 glyceryl isostearate, PEG-60 hydrogenated castor oil triisostearate, PPG-2-deceth-7, oleth-10, hydrogenated dimer dilinoleth-20, sorbitan cocoate, isosteareth-10, steareth-11, PEG-30 trimethylolpropane trimyristate, PEG-40 hydrogenated castor oil isostearate, PEG-40 hydrogenated castor oil PCA isostearate, laureth-7, isoceteth-10, ceteth-10, PEG-10 isostearate, PEG-10 stearate, PEG-10 oleate, PEG-10 glyceryl stearate, oleth-12, decyltetradeceth-15, choleth-15, PEG-16 dilaurate, PEG-30 hydrogenated castor oil, PEG-40 glyceryl triisostearate, PEG-40 glyceryl trioleate, PEG-40 trimethylolpropane triisostearate, PEG-40 hydrogenated castor oil laurate, and PEG-12 laurate.

In the present invention, the amount of the surfactant contained is, for example, 1% by mass to 20% by mass, preferably 1% by mass to 10% by mass, and more preferably 1% by mass to 5% by mass with respect to the total mass of an obtained solid base material for skin external application.

Note that the surfactant used in the present invention is at least one of the above-mentioned surfactants, and these surfactants may be used alone or two or more of them may be used in combination.

<1,2-Alkanediol, 1,3-Alkanediol, or Glycerol>

The above-mentioned solid base material for skin external application may contain a 1,2-alkanediol and a 1,3-alkanediol. The 1,2-alkanediol and the 1,3-alkanediol have a function of promoting the solubility of the above-mentioned lipid peptide compound.

Specific examples of the 1,2-alkanediols include 1,2-pentanediol, 1,2-hexanediol, 1,2-octanediol, and 1,2-decanediol. Preferred examples of the 1,2-alkanediols include 1,2-pentanediol, 1,2-hexanediol, and 1,2-octanediol. More preferably, 1,2-pentanediol or 1,2-hexanediol is employed. The 1,2-alkanediol used in the present invention is at least one of the above-mentioned 1,2-alkanediols, and these 1,2-alkanediols may be used alone or two or more of them may be used in combination.

Specific examples of the 1,3-alkanediols include 2-ethyl-1,3-hexanediol and 1,3-butanediol. Preferably, 2-ethyl-1,3-hexanediol is employed. The 1,3-alkanediol used in the present invention is at least one of the above-mentioned 1,3-alkanediols, and these 1,3-alkanediols may be used alone or two or more of them may be used in combination.

Furthermore, in the above-mentioned solid base material for skin external application, besides the above-mentioned 1,2-alkanediol and 1,3-alkanediol, glycerol may be preferably used as an ingredient having the function of promoting the solubility of the lipid peptide compound. Note that some commercially available products of the above-mentioned surfactants contain glycerol as a solvent, and in the case where such a commercially available product is used, glycerol contained as an ingredient also similarly acts to promote the solubility of the lipid peptide compound.

In the present invention, the amount of the 1,2-alkanediol, 1,3-alkanediol, or glycerol contained is, for example, 1% by mass to 20% by mass, preferably 1% by mass to 10% by mass, and more preferably 1% by mass to 5% by mass with respect to the total mass of an obtained solid base material for skin external application.

[Fatty Acid]

The above-mentioned solid base material for skin external application may further comprise a fatty acid. The fatty acid used in the present invention is preferably at least one selected from the group consisting of saturated and unsaturated fatty acids having a carbon atom number of 10 to 20, and salts of these fatty acids, and examples of the fatty acid include capric acid, undecanoic acid, lauric acid, tridecanoic acid, myristic acid, pentadecanoic acid, palmitic acid, margaric acid, and stearic acid. More preferred examples of the fatty acid include capric acid, lauric acid, myristic acid, palmitic acid, and stearic acid, and among these, stearic acid is the most preferable.

In the present invention, the amount of the fatty acid contained is, for example, 0.1% by mass to 2.0% by mass, and preferably 0.2% by mass to 1.0% by mass with respect to the total mass of an obtained solid base material for skin external application.

Note that the fatty acid used in the present invention is at least one of the above-mentioned fatty acids, and these fatty acids may be used alone or two or more of them may be used in combination.

[Oleaginous Base]

The above-mentioned solid base material for skin external application may further comprise an oleaginous base. Preferred examples of the oleaginous base used in the present invention include higher (polyhydric) alcohols, such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diols; aralkyl alcohols, such as benzyl alcohol, and derivatives thereof; isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteiso-henicosanoic acid, a branched long-chain fatty acid, dimer acid, and hydrogenated dimer acid; hydrocarbons, such as liquid paraffin (mineral oil), heavy liquid isoparaffin, light liquid isoparaffin, α-olefin oligomers, polyisobutenes, hydrogenated polyisobutene, polybutene, squalane, squalane derived from olive, squalene, vaseline, and solid paraffin; waxes, such as candelilla wax, carnauba wax, rice wax, Japan wax, beeswax, montan wax, ozokerite, ceresin, paraffin wax, microcrystalline wax, petrolatum, Fischer-Tropsch Wax, polyethylene wax, and an ethylene-propylene copolymer; vegetable oils and fats, such as coconut oil, palm oil, palm kernel oil, safflower oil, olive oil, castor oil, avocado oil, sesame oil, tea oil, evening primrose oil, wheat germ oil, macadamia nut oil, hazelnut oil, kukui nut oil, rose hip oil, meadowfoam oil, persic oil, tea tree oil, peppermint oil, corn oil, rapeseed oil, sunflower oil, wheat germ oil, linseed oil, cottonseed oil, soybean oil, peanut oil, rice bran oil, cacao butter, shea butter, hydrogenated coconut oil, hydrogenated castor oil, jojoba oil, and hydrogenated jojoba oil; animal oils and fats, such as beef tallow, milk fat, horse fat, egg-yolk oil, mink oil, and turtle oil; animal waxes, such as spermaceti, lanolin, and orange roughy oil; lanolins, such as liquid lanolin, reduced lanolin, adsorption-purified lanolin, acetylated lanolin, acetylated liquid lanolin, hydroxylated lanolin, polyoxyethylene lanolins, lanolin fatty acids, hard lanolin fatty acids, lanolin alcohol, acetylated lanolin alcohol, and acetylated (cetyl/lanolyl) ester; sterols, such as cholesterol, dihydrocholesterol, lanosterol, dihydrolanosterol, phytosterol, and cholic acid; sapogenins; saponins; sterol esters, such as cholesteryl acetate, cholesteryl nonanoate, cholesteryl stearate, cholesteryl isostearate, cholesteryl oleate, di(cholesteryllbehenyl/octyldodecyl)N-lauroyl-L-glutamate, di(cholesteryl/octyldodecyl) N-lauroyl-L-glutamate, di(phytosteryl/behenyl/octyldodecyl)N-lauroyl-L-glutamate, di(phytosteryl/octyldodecyl)N-lauroyl-L-glutamate, acyl sarcosine alkyl esters such as isopropyl N-lauroylsarcosinate, cholesteryl 12-hydroxystearate, cholesteryl macadamiate, phytosteryl macadamiate, phytosteryl isostearate, soft lanolin fatty acid cholesteryl esters, hard lanolin fatty acid cholesteryl esters, branched long-chain fatty acid cholesteryl esters, and long-chain α-hydroxy fatty acid cholesteryl esters; lipid complexes, such as a phospholipid-cholesterol complex and a phospholipid-phytosterol complex; monohydric alcohol carboxylic esters, such as octyldodecyl myristate, hexyldecyl myristate, octyldodecyl isostearate, cetyl palmitate, octyldodecyl palmitate, cetyl octanoate, hexyldecyl octanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocadate, isopropyl myristate, isopropyl palmitate, octyl palmitate, isopropyl isostearate, isopropyl lanolate, diethyl sebacate, diisopropyl sebacate, dioctyl sebacate, diisopropyl adipate, dibutyloctyl sebacate, diisobutyl adipate, dioctyl succinate, and triethyl citrate; oxyacid esters, such as cetyl lactate, diisostearyl malate, and hydrogenated castor oil monoisostearate; polyhydric alcohol fatty acid esters, such as glyceryl trioctanoate (glyceryl tri-2-ethylhexanoate), glyceryl trioleate, glyceryl triisostearate, glyceryl diisostearate, caprylic/capric triglyceride, caprylic/capric/myristic/stearic triglyceryl, hydrogenated rosin triglyceride (hydrogenated ester gum), rosin triglyceride (ester gum), glyceryl behenate eicosanedioate, trimethylolpropane trioctanoate, trimethyloipropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, hydrogenated rosin pentaerythrityl ester, ditrimethylolpropane triethylhexanoate, ditrimethylolpropane isostearate/sebacate, pentaerythrityl triethylhexanoate, dipentaerythrityl hydroxystearate/stearate/rosinate, diglyceryl diisostearate, polyglyceryl tetraisostearates, polyglyceryl-10 nonaisostearates, polyglyceryl-8 deca(erucate/isostearate/resinate)s, (hexyldecanoic acid/sebacic acid) diglyceryl oligoesters, glycol distearate (ethylene glycol distearate), 3-methyl-1,5-pentanediol dineopentanoate, and 2,4-diethyl-1,5-pentanediol dineopentanoate; dimer acid derivatives or dimer diol derivatives, such as diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensates, hydrogenated castor oil dimer dilinoleate, and hydroxyalkyl dimer dilinoleyl ethers; fatty acid alkanolamides, such as coconut oil fatty acid monoethanolamides (cocamide MEA), coconut oil fatty acid diethanolamides (cocamide DEA), lauric acid monoethanolamides (lauramide MEA), lauric acid diethanolamides (lauramide DEA), lauric acid monoisopropanolamides (lauramide MIPA), palmitic acid monoethanolamides (palmitamide MEA), palmitic acid diethanolamides (palmitamide DEA), and coconut oil fatty acid methylethanolamides (cocamide methyl MEA); silicones, such as dimethicone (dimethylpolysiloxane), highly-polymerized dimethicones (highly-polymerized dimethylpolysiloxane), cyclomethicone (cyclic dimethylsiloxane, decamethylcyclopentasiloxane (also simply referred to as cyclopentasiloxane)), phenyl trimethicone, diphenyl dimethicone, phenyl dimethicone, stearoxypropyldimethylamine, (aminoethylaminopropyl methicone/dimethicone) copolymers, dimethiconol, dimethiconol crosspolymers, a silicone resin, a silicone rubber, amino-modified silicones such as an aminopropyl dimethicone and an amodimethicone, cation-modified silicones, polyether-modified silicones such as dimethicone copolyols, polyglycerol-modified silicones, sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified and polyether-modified silicones, amino-modified and polyether-modified silicones, alkyl-modified and polyether-modified silicones, and polysiloxane-oxyalkylene copolymers; and fluorine-based oils, such as perfluorodecane, perfluorooctane, and perfluoropolyethers.

In the present invention, the amount of the oleaginous base contained is, for example, 1% by mass to 50% by mass, preferably 5% by mass to 50% by mass, more preferably 10% by mass to 50% by mass with respect to the total mass of an obtained solid base material for skin external application.

Note that the oleaginous base used in the present invention is at least one of the above-mentioned oleaginous bases, and these oleaginous bases may be used alone or two or more of them may be used in combination.

The above-mentioned solid base material for skin external application may further comprise polyethylene glycols. The contained polyethylene glycol allows the temporal stability of the solid base material for skin external application to be improved. As the above-mentioned polyethylene glycol, a polyethylene glycol, for example, having an average molecular weight of 1,000 to 4,000 may be preferably used.

In the present invention, the amount of the polyethylene glycol contained is, for example, 1% by mass to 20% by mass, and preferably 1% by mass to 10% by mass with respect to the total mass of an obtained solid base material for skin external application.

[Other Additives]

The above-mentioned solid base material for skin external application may contain an additive generally usable as an additive for cosmetics, an additive for quasi drugs, or an additive for pharmaceuticals, as necessary. Examples of additive ingredients such as a physiologically active substance and a functional substance that are contained in skin external preparations such as cosmetics, quasi drugs, and pharmaceuticals include a moisturizer, a texture improver, a surfactant other than the above, a polymer, a thickener/gelator, a solvent, a propellant, an antioxidant, a reducing agent, an oxidizing agent, a chelating agent, powder, an inorganic salt, an ultraviolet absorber, a whitening agent, vitamins and derivatives thereof, a hair growth-promoting agent, a blood circulation promoter, a stimulant, hormones, an anti-wrinkle agent, an anti-aging agent, a firming agent, a cooling agent, a warming agent, a wound-healing promoter, an abirritant, an analgesic, a cell activator, plant/animal/microbial extracts, a cuticle peeling/dissolving agent, an antiperspirant, a refrigerant, a styptic, an enzyme, a nucleic acid, a perfume, a coloring agent, a colorant, a dye, a pigment, an antiphlogistic, an anti-inflammatory agent, an anti-asthmatic agent, a therapeutic agent for chronic obstructive pulmonary disease, an antiallergic agent, and immunomodulator.

The amount of these additives blended may change depending on the kinds of the additives, but may be, for example, approximately 0.1% to 20% by mass, or 0.5% to 10% by mass with respect to the total mass of an obtained solid base material for skin external application.

Preferred examples of the moisturizer and the texture improver include polyols and polymers thereof, such as glycerol, trimethylolpropane, pentaerythritol, hexylene glycol, diglycerol, polyglycerols, diethylene glycol, dipropylene glycol, polypropylene glycols, and an ethylene glycol-propylene glycol copolymer; glycol alkyl ethers, such as diethylene glycol monoethyl ether (ethoxydiglycol), ethylene glycol monoethyl ether, ethylene glycol monobutyl ether, and diethylene glycol dibutyl ether; water-soluble esters, such as polyglyceryl-10 (eicosanedioates/tetradecanedioates) and polyglyceryl-10 tetradecanedioates; sugar alcohols, such as sorbitol, xylitol, erythritol, mannitol, and maltitol; sugars and derivatives thereof, such as glucose, fructose, galactose, mannose, threose, xylose, arabinose, fucose, ribose, deoxyribose, maltose, trehalose, lactose, raffinose, gluconic acid, glucuronic acid, cyclodextrins ($\alpha$-, $\beta$-, and $\gamma$-cyclodextrins, and modified cyclodextrins such as maltosyl cyclodextrin and hydroxyalkyl cyclodextrins), $\beta$-glucan, chitin, chitosan, heparin and derivatives thereof, pectin, arabinogalactan, dextrin, dextran, glycogen, ethyl glucoside, a glucosylethyl methacrylate polymer or copolymer; hyaluronic acid and sodium hyaluronate; sodium chondroitin sulfate; mucoitin sulfate, chaoronin sulfate, kerato sulfate, and dermatan sulfate; a Tremella fuciformis extract and Tremella fuciformis polysaccharides; fucoidan; tuberose polysaccharides or natural polysaccharides; organic acids and salts thereof, such as citric acid, tartaric acid, and lactic acid; urea and derivatives thereof; 2-pyrrolidone-5-carboxylic acid, and salts such as a sodium salt thereof; amino acids and salts thereof, such as betaine (trimethylglycine), proline, hydroxyproline, arginine, lysine, serine, glycine, alanine, phenylalanine, tyrosine, $\beta$-alanine, threonine, glutamic acid, glutamine, asparagine, aspartic acid, cysteine, methionine, leucine, isoleucine, valine, tryptophan, histidine, and taurine; protein peptides and derivatives thereof, such as collagen, fish collagen, atelocollagen, gelatin, elastin, peptides derived from decomposed collagen, hydrolyzed collagen, hydroxypropylammonium chloride hydrolyzed collagen, peptides derived from decomposed elastin, peptides derived from decomposed keratin, hydrolyzed keratin, peptides derived from decomposed conchiolin, hydrolyzed conchiolin, peptides derived from decomposed silk protein, hydrolyzed silk, sodium lauroyl hydrolyzed silk, peptides derived from decomposed soy protein, peptides derived from decomposed wheat protein, hydrolyzed wheat protein, peptides derived from decomposed casein, and acylated peptides; acylated peptides, such as a palmitoyl oligopeptide, palmitoyl pentapeptide, and palmitoyl tetrapeptide; silylated peptides; a culture medium of lactic acid bacteria, a yeast extract solution, eggshell membrane protein, bovine submaxillary mucin, hypotaurine, sesame lignan glycosides, glutathione, albumin, and whey; choline chloride and phosphorylcholine; and animal and plant extract components, such as a placenta extract solution, elastin, collagen, an aloe extract, *Hammamelis virginiana* water, *Luffa cylindrica* water, a *Chamomilla recutita* extract, a licorice extract, comfrey extract, a silk extract, a *Rosa roxburghii* extract, an *Achillea millefolium* extract, an *Eucalyptus globulus* extract, and a melilot extract, and ceramides, such as natural ceramides (types 1, 2, 3, 4, 5, and 6), hydroxyceramide, pseudoceramide, sphingoglycolipid, a ceramide-containing extract, and a glucosylceramide-containing extract.

Preferred examples of the surfactant include an anionic surfactant, a nonionic surfactant, a cationic surfactant, an amphoteric surfactant, and a polymer surfactant. The preferred surfactants are exemplified below. Preferred examples of the anionic surfactant include fatty acid salts, such as potassium laurate and potassium myristate; alkylsulfuric acid ester salts, such as sodium lauryl sulfate, triethanolamine lauryl sulfate, and ammonium lauryl sulfate; polyoxyethylene alkylsulfates, such as sodium laureth sulfate and triethanolamine laureth sulfate; acyl N-methylamino acid salts, such as sodium cocoyl methyl taurate, potassium cocoyl methyl taurate, sodium lauroyl methyl taurate, sodium myristoyl methyl taurate, sodium lauroyl methylalaninate, sodium lauroyl sarcosinate, triethanolamine lauroyl sarcosinate, and sodium lauroyl glutamate methylalaninate; acyl amino acid salts, such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates, such as sodium laureth acetate; succinic acid ester salts, such as sodium lauroyl monoethanolamide succinate; fatty acid alkanolamide ether carboxylates; acyl lactates;

polyoxyethylene fatty amine sulfates; fatty acid alkanolamide sulfates; fatty acid glyceride sulfates, such as glycerol hydrogenated coconut oil fatty acid sulfate sodium salts; alkylbenzene polyoxyethylene sulfates; olefin sulfonates, such as sodium α-olefin sulfonate; alkyl sulfosuccinates, such as disodium lauryl sulfosuccinate and sodium dioctyl sulfosuccinate; alkyl ether sulfosuccinates, such as disodium laureth sulfosuccinate, sodium monolauroyl monoethanolamide polyoxyethylene sulfosuccinates, and sodium lauryl polypropylene glycol sulfosuccinates; alkylbenzene sulfonates, such as sodium tetradecylbenzene sulfonate and triethanolamine tetradecylbenzene sulfonate; alkyl naphthalene sulfonates; alkane sulfonates; α-sulfofatty acid methyl ester salts; acyl isethionates; alkyl glycidyl ether sulfonates; alkyl sulfoacetate; alkyl ether phosphates, such as sodium laureth phosphate, sodium dilaureth phosphate, sodium trilaureth phosphate, and sodium monooreth phosphate; alkyl phosphates, such as potassium lauryl phosphate; sodium caseinate; alkyl aryl ether phosphates; fatty acid amide ether phosphates; phospholipids, such as phosphatidylglycerol, phosphatidylinositol, and phosphatidic acid; and silicone anionic surfactants, such as carboxylic acid-modified silicone, phosphoric acid-modified silicone, and sulfuric acid-modified silicone. Preferred examples of the nonionic surfactant include polyoxyethylene alkyl ethers having various numbers of polyoxyethylenes, such as laureths (polyoxyethylene lauryl ethers), ceteths (polyoxyethylene cetyl ethers), steareths (polyoxyethylene stearyl ethers), beheneths (polyoxyethylene behenyl ethers), isosteareths (polyoxyethylene isostearyl ethers), and octyldodeceths (polyoxyethylene octyldodecyl ethers); polyoxyethylene alkyl phenyl ethers; castor oil derivatives and hydrogenated castor oil derivatives, such as polyoxyethylene hydrogenated castor oils, polyoxyethylene castor oils, polyoxyethylene hydrogenated castor oil monoisostearates, polyoxyethylene hydrogenated castor oil triisostearates, polyoxyethylene hydrogenated castor oil monopyroglutamate monoisostearate diesters, and polyoxyethylene hydrogenated castor oil maleates; polyoxyethylene phytosterols; polyoxyethylene cholesterols; polyoxyethylene cholestanols; polyoxyethylene lanolins; polyoxyethylene reduced lanolins; polyoxyethylene-polyoxypropylene alkyl ethers, such as polyoxyethylene-polyoxypropylene cetyl ethers, polyoxyethylene-polyoxypropylene 2-decyltetradecyl ethers, polyoxyethylene-polyoxypropylene monobutyl ethers, polyoxyethylene-polyoxypropylene hydrogenated lanolins, and polyoxyethylene-polyoxypropylene glycerol ethers; polyoxyethylene-polyoxypropylene glycols; (poly)glycerol polyoxypropylene glycols, such as PPG-9 diglyceryl; glycerol fatty acid partial esters, such as glyceryl stearate, glyceryl isostearate, glyceryl palmitate, glyceryl myristate, glyceryl oleate, glyceryl cocoate, glycerol mono-cottonseed oil fatty acid esters, glycerol monoerucate, glycerol sesquioleate, glycerol α, α'-oleate pyroglutamate, and glycerol monostearate malate; polyglycerol fatty acid esters, such as polyglyceryl-2 stearates, polyglyceryl-3 stearates, polyglyceryl-4 stearates, polyglyceryl-5 stearates, polyglyceryl-6 stearates, polyglyceryl-8 stearates, polyglyceryl-10 stearates, polyglyceryl-6 distearates, polyglyceryl-10 distearates, polyglyceryl-2 tristearates, polyglyceryl-10 decastearates, polyglyceryl-2 isostearates, polyglyceryl-3 isostearates, polyglyceryl-4 isostearates, polyglyceryl-5 isostearates, polyglyceryl-6 isostearates, polyglyceryl-8 isostearates, polyglyceryl-10 isostearates, polyglyceryl-2 diisostearates (diglyceryl diisostearate), polyglyceryl-3 diisostearates, polyglyceryl-10 diisostearates, polyglyceryl-2 triisostearates, polyglyceryl-2 tetraisostearates, polyglyceryl-10 decaisostearates, polyglyceryl-2 oleates, polyglyceryl-3 oleates, polyglyceryl-4 oleates, polyglyceryl-5 oleates, polyglyceryl-6 oleates, polyglyceryl-8 oleates, polyglyceryl-10 oleates, polyglyceryl-6 dioleates, polyglyceryl-2 trioleates, and polyglyceryl-10 decaoleates; ethylene glycol mono-fatty acid esters, such as ethylene glycol monostearate; propylene glycol mono-fatty acid esters, such as propylene glycol monostearate; pentaerythritol fatty acid partial esters; sorbitol fatty acid partial esters; maltitol fatty acid partial esters; maltitol ether; sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, sorbitan penta-2-ethylhexylate diglycerol, and sorbitan tetra-2-ethylhexylate diglycerol; sugar derivative partial esters, such as sucrose fatty acid esters, methyl glucoside fatty acid esters, and trehalose undecylenoate; alkyl glucosides, such as caprylyl glucoside; alkyl polyglycosides; lanolin alcohol; reduced lanolin; polyoxyethylene fatty acid monoesters and diesters, such as polyoxyethylene distearates, polyethylene glycol diisostearates, polyoxyethylene monooleates, and polyoxyethylene dioleates; polyoxyethylene-propylene glycol fatty acid esters; polyoxyethylene glycerol fatty acid esters, such as polyoxyethylene monooleates such as polyoxyethylene glycerol monostearates, polyoxyethylene glycerol monoisostearates, and polyoxyethylene glycerol triisostearates; polyoxyethylene sorbitan fatty acid esters, such as polyoxyethylene sorbitan monooleates, polyoxyethylene sorbitan monostearates, polyoxyethylene sorbitan monooleates, and polyoxyethylene sorbitan tetraoleates; polyoxyethylene sorbitol fatty acid esters, such as polyoxyethylene sorbitol monolaurates, polyoxyethylene sorbitol monooleates, polyoxyethylene sorbitol pentaoleates, and polyoxyethylene sorbitol monostearates; polyoxyethylene methyl glucoside fatty acid esters; polyoxyethylene alkyl ether fatty acid esters; polyoxyethylene-modified animal and vegetable fats and oils, such as polyoxyethylene sorbitol beeswax; alkyl glyceryl ethers, such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants, such as saponin and sophorolipid; polyoxyethylene fatty acid amides; fatty acid alkanolamides, such as coconut oil fatty acid monoethanolamides (cocamide MEA), coconut oil fatty acid diethanolamides (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamides (cocamide methyl MEA); alkyl dimethylamine oxides, such as lauramine oxide, cocamine oxide, stearamine oxide, and behenamine oxide; alkyl ethoxydimethylamine oxides; polyoxyethylene alkyl mercaptans; and silicone nonionic surfactants, such as polyether-modified silicones such as dimethicone copolyols, a polysiloxane-oxyalkylene copolymer, polyglycerol-modified silicones, and sugar-modified silicones. Preferred examples of the cationic surfactant include alkyl trimethylammonium chlorides, such as behentrimonium chloride, steartrimonium chloride, cetrimonium chloride, and lauryltrimonium chloride; alkyl trimethylammonium bromides, such as steartrimonium bromide; dialkyl dimethylammonium chlorides, such as distearyldimonium chloride and dicocodimonium chloride; fatty acid amide amines, such as stearamidopropyl dimethylamine and stearamidoethyldiethylamine, and salts thereof; alkyl ether amines, such as stearoxypropyldimethylamine, and salts or quaternary salts thereof; fatty acid amide quaternary ammonium salts, such as branched long-chain fatty acid (12 to 31) aminopropylethyldimethylammonium ethyl sulfates and lanolin fatty acid aminopropylethyldimethylammonium ethyl sulfates; polyoxyethylene alkylamines, and salts or quaternary salts thereof; alkylamine salts; fatty acid amide guanidium salts; alkyl ether ammonium salts; alkyl trialkylene glycol ammonium salts; benzalkonium salts; benzethonium salts; pyridinium salts, such as cetylpyridinium chloride; imidazolinium salts; alkyl isoquinolinium salts; dialkyl morpholinium salts; polyamine fatty acid derivatives; and silicone cationic surfactants, such as amino-modified silicone such as aminopropyl dimethicone and amodimethicone, cation-modified silicone, cation-modified and polyether-modified silicones, and amino-modified and polyether-modified silicones. Preferred examples of the amphoteric surfactant include N-alkyl-N,N-dimethylamino acid betaines, such as lauryl betaine (lauryl dimethylaminoacetic acid betaine); fatty acid amido alkyl-N,N-dimethylamino acid betaines, such as cocamide propyl betaine and lauramide propyl betaine; imidazoline betaines, such as sodium cocoamphoacetate and sodium lauroamphoacetate; alkyl sulfobetaines, such as alkyl dimethyltaurines; betaine sulfates, such as alkyl dimethylarninoethanol sulfates; betaine phosphates, such as alkyl dimethylaminoethanol phosphates; phospholipids, such as phosphatidylcholine, phosphatidylethanolamine, phosphatidylserine, sphingophospholipids such as sphingomyelin, lysolecithin, hydrogenated soybean phospholipid, partially hydrogenated soybean phospholipid, hydrogenated egg yolk phospholipid, partially hydrogenated egg yolk phospholipid, and hydroxylated lecithin; and silicone amphoteric surfactants. Preferred examples of the polymer surfactant include polyvinyl alcohols, sodium alginate, starch derivatives, tragacanth gum, and an acrylic acid-alkyl methacrylate copolymer; and various silicone surfactants.

A polymer, a thickener, and a gelator may be blended in for the purpose of improving formulation properties and feeling after use, such as gel viscosity adjustment, moisturizing effect, coating effect, and feeling adjustment. Specific preferred examples of the polymer, the thickener, and the gelator include guar gum, locust bean gum, quince seed, carrageenan, galactan, gum arabic, tara gum, tamarind, furcellaran, karaya gum, *Abelmoschus manihot*, cara gum, tragacanth gum, pectin, pectic acid and salts thereof such as a sodium salt thereof, alginic acid and salts thereof such as a sodium salt thereof, mannan; starches, such as rice starch, corn starch, potato starch, and wheat starch; xanthan gum, dextran, succinoglucan, curdlan, hyaluronic acid and salts thereof, xanthan gum, pullulan, gellan gum, chitin, chitosan, agar, a brown algae extract, chondroitin sulfate, casein, collagen, gelatin, albumin; cellulose and derivatives thereof, such as methyl cellulose, ethyl cellulose, hydroxyethyl cellulose, hydroxypropyl cellulose, hydroxypropyl methylcellulose, carboxymethyl cellulose and salts thereof such as a sodium salt thereof, methylhydroxypropyl cellulose, sodium cellulose sulfate, dialkyldimethylammonium cellulose sulfate, crystalline cellulose, and cellulose powder; starch derivatives, such as soluble starch, starch polymers such as carboxymethyl starch, methylhydroxypropyl starch, and methyl starch, starch hydroxypropyltrimonium chloride, and aluminum corn starch octenylsuccinate; alginic acid derivatives, such as sodium alginate and propylene glycol alginate; polyvinyl pyrrolidones (PVP), polyvinyl alcohols (PVA), a vinylpyrrolidone-vinyl alcohol copolymer, polyvinyl methyl ethers; polyethylene glycols, polypropylene glycols, and a polyoxyethylene-polyoxypropylene copolymers; amphoteric methacrylic ester copolymers, such as a (methacryloyloxyethylcarboxybetaine/alkyl methacrylate) copolymer and an (acrylate/stearyl acrylate/ethylamine oxide methacrylate) copolymer; a (dimethicone/vinyl dimethicone) crosspolymer, an (alkyl acrylate/diacetone acrylamide) copolymer, and an (alkyl acrylate/diacetone acrylamide) copolymer AMP; a partially saponified polyvinyl acetate, a maleic acid copolymer; a vinylpyrrolidone-dialkylaminoalkyl methacrylate copolymer; an acrylic resin alkanolamine; polyesters, water-dispersible polyesters; polyacrylamides; a copolymer of a polyacrylic ester such as polyethyl acrylate, a carboxy vinyl polymer, polyacrylic acid and salts thereof such as a sodium salt thereof, an acrylic acid-methacrylic acid ester copolymer; an acrylic acid-alkyl methacrylate copolymer; cationized cellulose such as a polyquaternium-10, a diallyldimethylammonium chloride-acrylamide copolymer such as a polyquaternium-7, an acrylic acid-diallyldimethylammonium chloride copolymer such as a polyquaternium-22, an acrylic acid-diallyldimethylanimonium chloride-acrylamide copolymer such as a polyquaternium-39, an acrylic acid-cationized methacrylic ester copolymer, an acrylic acid-cationized methacrylic amide copolymer, an acrylic acid-methyl acrylate-methacrylamidopropyltrimethylammonium chloride copolymer such as a polyquaternium-47, a methacryloyl chloride choline ester polymer; cationized polysaccharides, such as a cationized oligosaccharide, cationized dextran, and guar hydroxypropyltrimonium chloride; polyethyleneimines; a cationic polymer; a copolymer of a 2-methacryloyloxyethyl phosphorylcholine polymer and a butyl methacrylate copolymer, such as a polyquatemium-51; polymer emulsions, such as an acrylic resin emulsion, a polyethyl acrylate emulsion, a polyacrylalkyl ester emulsion, a polyvinyl acetate resin emulsion, a natural rubber latex, and a synthetic latex; nitrocellulose; polyurethanes and various copolymers thereof; various silicones; various silicone-based copolymers, such as an acrylic-silicone graft copolymer; various fluorine-based polymers; 12-hydroxystearic acid and salts thereof; dextrin fatty acid esters, such as dextrin palmitate and dextrin myristate; silicic anhydride, fumed silica (silicic anhydride ultrafine particles), magnesium aluminum silicate, magnesium sodium silicate, a metallic soap, a metal dialkyl phosphate, bentonite, hectorite, organo-modified clay mineral, a sucrose fatty acid ester, and a fructooligosaccharide fatty acid ester. Among these examples, cellulose and derivatives thereof, alginic acid and salts thereof, polyvinyl alcohols, hyaluronic acid and salts thereof, and collagen are more preferable.

Preferred examples of the solvents and the propellants include lower alcohols, such as ethanol, 2-propanol (isopropyl alcohol), butanol, and isobutyl alcohol; glycols, such as propylene glycol, diethylene glycol, dipropylene glycol, and isopentyldiol; glycol ethers, such as diethylene glycol monoethyl ether (ethoxy diglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters, such as ethylene glycol monoethyl ether acetate, diethylene glycol monoethyl ether acetate, and propylene glycol monoethyl ether acetate; glycol esters, such as diethoxyethyl succinate and ethylene glycol disuccinate; benzyl alcohol, benzyloxyethanol, propylene carbonate, dialkyl carbonate, acetone, ethyl acetate, and N-methylpyrrolidone; toluene; fluorocarbon, and next-generation fluorocarbon; and propellants such as LPG, dimethyl ether, and carbon dioxide gas.

Preferred examples of the antioxidant include tocopherol (vitamin E), and tocopherol derivatives such as tocopherol acetate; BHT, and BHA; gallic acid derivatives, such as propyl gallate; vitamin C (ascorbic acid) and/or derivatives thereof; erythorbic acid and derivatives thereof; sulfites, such as sodium sulfite; hydrogen sulfites, such as sodium hydrogen sulfite; thiosulfates, such as sodium thiosulfate; hydrogen metasulfites; thiotaurine, and hypotaurine; and thioglycerol, thiourea, thioglycolic acid, and cysteine hydrochloride.

Preferred examples of the reducing agent include thioglycolic acid, cysteine, and cysteamine.

Preferred examples of the oxidizing agent include an hydrogen peroxide solution, ammonium persulfate, sodium bromate, and percarbonic acid.

Preferred examples of the chelating agent include edetates (ethylenediamine tetraacetates), such as EDTA, EDTA-2Na, EDTA-3Na, and EDTA-4Na; hydroxyethylethylenediamine triacetates, such as HEDTA-3Na; pentetates (diethylenetriamine pentaacetate); phytic acid; phosphonic acids such as etidronic acid, and salts such as a sodium salt thereof; polyamino acids, such as polyaspartic acids and polyglutamic acids; sodium polyphosphates, sodium metaphosphate, and phosphoric acid; and sodium citrate, citric acid, alanine, dihydroxyethylglycine, gluconic acid, ascorbic acid, succinic acid, and tartaric acid.

Preferred examples of the powder include inorganic powder having various sizes and shapes, such as mica, talc, kaolin, sericite, montmorillonite, kaolinite, mica, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium, zeolite, barium sulfate, calcined calcium sulfate, calcium phosphate, fluorapatite, hydroxyapatite, ceramic powder, bentonite, smectite, clay, mud, metallic soaps (for example, zinc myristate, calcium palmitate, and aluminum stearate), calcium carbonate, red iron oxide, yellow iron oxide, black iron oxide, ultramarine, prussian blue, carbon black, titanium oxide, titanium oxide fine particles and titanium oxide ultrafine particles, zinc oxide, zinc oxide fine particles and zinc oxide ultrafine particles, alumina, silica, fumed silica (silicic anhydride ultrafine particles), titanated mica, fish scale, boron nitride, photochromic pigments, synthetic fluorophlogopite, particulate composite powder, gold, and aluminum, and inorganic powder, such as hydrophobic or hydrophilic powder, obtained by treatment of the above-exemplified powder with various surface treating agents such as silicones, such as hydrogen silicone and cyclic hydrogen silicone, other silanes, or titanium coupling agents; and organic powder, surface-treated powder, and organic-inorganic composite powder, each having various sizes and shapes, such as starch, cellulose, nylon powder, polyethylene powder, polymethyl methacrylate powder, polystyrene powder, styrene-acrylic acid copolymer resin powder, polyester powder, benzoguanamine resin powder, polyethylene terephthalate-polymethyl methacrylate laminated powder, polyethylene terephthalate-aluminum-epoxy laminated powder, urethane powder, silicone powder, and Teflon (registered trademark) powder.

Preferred examples of the inorganic salts include sodium chloride-containing salts, such as common salt, regular salt, rock salt, sea salt, and natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as mono-, di-, and tri-sodium phosphates, potassium phosphates, calcium phosphates, and magnesium phosphates.

Preferred examples of the ultraviolet absorber include benzoate ultraviolet absorbers, such as p-aminobenzoic acid, p-aminobenzoic acid monoglycerol ester, N,N-dipropoxy-p-aminobenzoic acid ethyl ester, N,N-diethoxy-p-aminobenzoic acid ethyl ester, N,N-dimethyl-p-aminobenzoic acid ethyl ester, N,N-dimethyl-p-aminobenzoic acid butyl ester, and N,N-dimethyl-p-aminobenzoic acid ethyl ester; anthranilate ultraviolet absorbers, such as homomenthyl-N-acetylanthranilate; salicylate ultraviolet absorbers, such as salicylic acid and a sodium salt thereof, amyl salicylate, menthyl salicylate, homomenthyl salicylate, octyl salicylate, phenyl salicylate, benzyl salicylate, and p-isopropanolphenyl salicylate; cinnamate ultraviolet absorbers, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate (octyl p-methoxycinnamate), 2-ethoxyethyl p-methoxycinnamate (cinoxate), cyclohexyl p-methoxycinnamate, ethyl α-cyano-β-phenylcinnamate, 2-ethylhexyl-α-cyano-β-phenylcinnamate (octocrylene), glyceryl mono-2-ethylhexanoyl di-p-methoxycinnamate, ferulic acid, and derivatives thereof; benzophenone ultraviolet absorbers, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; 3-(4'-methylbenzylidene)-d,l-camphor, and 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methyl-phenyl)benzotriazole; dibenzalazine; dianisoyltmethane; 5-(3,3-dimethyl-2-norbomylidene)-3-pentan-2-one; dibenzoylmethane derivatives, such as 4-t-butylmethoxydibenzoylmethane; octyl triazone; urocanic acid, and urocanic acid derivatives such as ethyl urocanate; and 2-(2'-hydroxy-5'-methylphenyl)benzotriazole, 1-(3,4-dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic acid, drometrizole trisiloxane, methyl anthranilate, rutin and derivatives thereof, and oryzanol and derivatives thereof.

Preferred examples of the whitening agent include hydroquinone glycosides such as arbutin and α-arbutin, and esters thereof, ascorbic acid, and ascorbic acid derivatives, such as ascorbyl phosphates such as sodium ascorbyl phosphate and magnesium ascorbyl phosphate, ascorbyl fatty acid esters such as ascorbyl tetraisopalmitate, ascorbic acid alkyl ethers such as ascorbic acid ethyl ether, ascorbic acid glucoside such as ascorbic acid 2-glucoside and fatty acid esters thereof, ascorbyl sulfate, and tocopheryl ascorbyl phosphate; and kojic acid, ellagic acid, tranexamic acid and derivatives thereof, ferulic acid and derivatives thereof, a placenta extract, glutathione, oryzanol, butylresocinol, and plant extracts such as an oil-soluble *Chamomilla recutita* extract, an oil-soluble licorice extract, a *Tamarix chinensis* extract, and a saxifrage extract.

Preferred examples of the vitamins and derivatives thereof include vitamin As, such as retinal, retinol acetate, and retinol palmitate; vitamin Bs, such as thiamine hydrochloride, thiamine sulfate, riboflavin, riboflavin acetate, pyridoxine hydrochloride, pyridoxine dioctanoate, pyridoxine dipalmitate, flavin adenine dinucleotide, cyanocobalamin, folic acids, nicotinic acids such as nicotinamide and benzyl nicotinate, and cholines; vitamin Cs, such as ascorbic acid and salts such as a sodium salt thereof; vitamin Ds; vitamin Es, such as α-, β-, γ-, and δ-tocopherols; other vitamins, such as pantothenic acid and biotin; ascorbic acid derivatives, such as ascorbyl phosphates such as sodium ascorbyl phosphate and magnesium ascorbyl phosphate, ascorbyl fatty acid esters such as ascorbyl tetraisopalmitate, ascorbyl stearate, ascorbyl palmitate, and ascorbyl dipalmitate, ascorbic acid alkyl ethers such as ascorbic acid ethyl ether, ascorbic acid glucosides such as ascorbic acid 2-glucoside and fatty acid esters thereof; and tocopheryl ascorbyl phosphate; vitamin derivatives, such as tocopherol derivatives such as tocopherol nicotinate, tocopherol acetate, tocopherol linoleate, tocopherol ferulate, and tocopherol phosphate, tocotrienol, and other various vitamin derivatives.

Preferred examples of the hair growth-promoting agent, the blood circulation-promoter, and the stimulant include plant extracts and tinctures, such as swertia herb extract, capsicum tincture, ginger tincture, ginger extract, and cantharis tincture; and capsaicin, nonylic acid vanillylamide, zingerone, ichthammol, tannic acid, borneol, cyclandelate, cinnarizine, tolazoline, acetylcholine, verapamil, cepharanthine, γ-oryzanol, vitamin E and derivatives thereof such as tocopherol nicotinate and tocopherol acetate, nicotinic acid and derivatives thereof such as nicotinamide, benzyl nicotinate, inositol hexanicotinate, and nicotinic alcohol, allantoin, Photosensitizing dye 301, Photosensitizing dye 401, carpronium chloride, pentadecanoic acid monoglyceride, flavanonol derivatives, stigmasterol and stigmastanol and glycosides thereof; and minoxidil.

Preferred examples of the hormones include estradiol, estrone, ethynylestradiol, cortisone, hydrocortisone, and prednisone. Preferred examples of other therapeutic agents such as the anti-wrinkle agent, the anti-aging agent, the firming agent, the cooling agent, the warming agent, the wound-healing promoter, the abirritant, the analgesic, and the cell activator include retinols, retinoic acids, and tocopheryl retinoate; lactic acid, glycolic acid, gluconic acid, fruit acid, salicylic acid, and derivatives such as glycosides and esters thereof, and α- or β-hydroxy acids and derivatives thereof, such as hydroxycapric acid, long-chain α-hydroxy fatty acids, and long-chain α-hydroxy fatty acid cholesteryl esters; γ-aminobutyric acid, and γ-amino-β-hydroxybutyric acid; carnitine; carnosine; creatine; ceramides, and sphingosines; caffeine, xanthine, and derivatives thereof; antioxidizing agents and active oxygen scavengers, such as coenzyme Q10, carotene, lycopene, astaxanthin, lutein, α-lipoic acid, platinum nanocolloide, and fullerenes; catechins; flavones, such as quercetin; isoflavones; gallic acid and sugar ester derivatives thereof; polyphenols, such as tannin, sesamin, proanthocyanidin, chlorogenic acid, and apple polyphenols; rutin and derivatives such as glycosides thereof; hesperidin and derivatives such as glycosides thereof, lignan glycosides; licorice extract related substances, such as glabridin, glabrene, liquiritin, and isoliquiritin; lactoferrin; shogaol, and gingerol; perfume substances, such as menthol and cedrol, and derivatives thereof; capsaicin and vanillin, and derivative thereof; insect repellents, such as diethyltoluamide; and complexes of a physiologically active substance and cyclodextrins.

Preferred examples of the plant, animal, and microbial extracts include extracts, such as iris extract, *Angelica keiskei* extract, *Thujopsis dolabrata* extract, asparagus extract, avocado extract, *Hydrangea serrata* extract, almond extract, *Althaea officinalis* extract, *Arnica montana* extract, aloe extract, apricot extract, apricot kernel extract, ginkgo extract, *Artemisia capillaris* flower extract, fennel seed extract, turmeric root extract, oolong tea extract, uva-ursi extract, rose fruit extract, *Echinacea angustifolia* leaf extract, *Isodonis japonicus* extract, scutellaria root extract, phellodendron bark extract, coptis rhizome extract, barley extract, *Panax ginseng* extract, hypericum extract, *Lamium album* extract, *Ononis spinosa* extract, *Nasturtium officinale* extract, orange extract, dried sea water residues, seaweed extract, Japanese persimmon leaf extract, *Pyracantha fortuneana* extract, hydrolyzed elastin, hydrolyzed wheat powder, hydrolyzed silk, pueraria root extract, *Chamomilla recutita* extract, oil-soluble *Chamomilla recutita* extract, carrot extract, *Artemisia capillaris* extract, *Avena fatua* extract, *Hibiscus sabdariffa* extract, licorice extract, oil-soluble licorice extract, kiwi fruit extract, kiou extract, jew's-ear extract, cinchona extract, cucumber extract, *Paulownia tomentosa* leaf extract, guanosine, guava extract, sophora root extract, *Gardenia jasminoides* extract, *Sasa veitchii* extract, *Sophora flavescens* extract, walnut extract, chestnut extract, grapefruit extract, *Clematis vitalba* extract, black rice extract, black sugar extract, black vinegar, chlorella extract, mulberry extract, gentian extract, geranium herb extract, black tea extract, yeast extract, magnolia bark extract, coffee extract, burdock root extract, rice extract, fermented rice extract, fermented rice bran extract, rice germ oil, comfrey extract, collagen, bilberry extract, asiasarum root extract, bupleurum root extract, umbilical cord extract solution, saffron extract, salvia extract, *Saponaria officinalis* extract, bamboo grass extract, *Crataegus cuneata* extract, *Bombyx mori* excrementum extract, zanthoxylum fruit extract, shiitake mushroom extract, rehmannia root extract, lithospermum root extract, *Perilla frutescens* extract, *Tilia japonica* extract, *Filipendula multijuga* extract, jatoba extract, peony root extract, ginger extract, *Acorns calamus* root extract, *Betula alba* extract, Tremella fuciformis extract, *Equisetum arvense* extract, stevia extract, stevia fermentation product, *Tamarix chinensis* extract, *Hedera helix* extract, *Crataegus oxycantha* extract, *Sambucus nigra* extract, *Achillea millefolium* extract, *Mentha piperita* extract, sage extract, mallow extract, cnidium rhizome extract, swertia herb extract, mulberry bark extract, rhubarb extract, soybean extract, jujubi extract, thyme extract, dandelion extract, lichens extract, tea extract, clove extract, *Imperata cylindrica* extract, *citrus unshiu* peel extract, tea tree oil, *Rubus suavissimus* extract, capsicum extract, Japanese angelica root extract, *Calendula officinalis* extract, peach kernel extract, bitter orange peel extract, *Houttuynia cordata* extract, tomato extract, natto extract, carrot extract, garlic extract, *Rosa multiflora* extract, hibiscus extract, ophiopogon tuber extract, lotus extract, parsley extract, birch extract, honey, *Hamamelis virginiana* extract, *Parietaria officinalis* extract, *Rabdosia japonica* extract, bisabolol, Japanese cypress extract, *Bifidobacterium* extract, loquat extract, coltsfoot extract, Japanese butterbur flower-bud extract, hoelen extract, *Ruscus aculeatus* extract, grape extract, grape seed extract, propolis, *Luffa cylindrica* extract, safflower extract, peppermint extract, *Tilia miqueliaria* extract, *Paeonia suffruticosa* extract, hop extract, *Rosa*

*rugosa* extract, pine extract, *Aesculus hippocastanum* extract, *Lysichiton camtschatcense* extract, *Sapindus mukurossi* extract, *Melissa officinalis* extract, *Nemacystus decipiens* extract, peach extract, cornflower extract, *Eucalyptus globulus* extract, saxifrage extract, *Citrus junos* extract, lily extract, coix seed extract, *Artemisia princeps* extract, lavender extract, green tea extract, egg shell membrane extract, apple extract, rooibos tea extract, *Litchi chinensis* extract, lettuce extract, lemon extract, forsythia fruit extract, *Astragalus sinicus* extract, rose extract, rosemary extract, *Anthemis nobilis* extract, royal jelly extract, and burnt extract.

Examples of the cuticle peeling and dissolving agent include salicylic acid, sulfur, resorcin, selenium sulfide, and pyridoxine.

Examples of the antiperspirant include aluminum chlorohydrate, aluminum chloride, zinc oxide, and zinc p-phenolsulfonate.

Examples of the refrigerant include menthol and methyl salicylate.

Examples of the styptic include citric acid, tartaric acid, lactic acid, aluminum potassium sulfate, and tannic acid.

Examples of the enzymes include superoxide dismutase, catalase, lysozyme chloride, lipase, papain, pancreatin, and protease.

Preferred examples of the nucleic acids include ribonucleic acids and salts thereof, deoxyribonucleic acids and salts thereof, and adenosine triphosphate disodium.

Preferred examples of the perfume include synthetic perfumes and natural perfumes, such as acetyl cedrene, amylcinnamaldehyde, allylamyl glycolate, β-ionone, Iso E Super, isobutylquinoline, iris oil, irone, indole, ylang-ylang oil, undecanal, undecenal, γ-undecalactone, estragole, eugenol, oakmoss, opoponax resinoid, orange oil, eugenol, aurantiol, galaxolide, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandalwood oil, santalol, cyclamen aldehyde, cyclopentadecanolide, methyl dihydrojasmonate, dihydromyrcenol, jasmine absolute, jasmine lactone, cis-jasmone, citral, citronellol, citronellal, cinnamon bark oil, 1,8-cineole, cinnamaldehyde, styrax resinoid, cedarwood oil, cedrene, cedrol, celery seed oil, thyme oil, damascone, damascenone, thymol, tuberose absolute, decanal, decalactone, terpineol, γ-terpinen, triplal, nerol, nonanal, 2,6-nonadienal, nonalactone, patchouli alcohol, vanilla absolute, vanillin, basil oil, patchouli oil, hydroxycitronellal, α-pinene, piperitone, phenethyl alcohol, phenylacetaldehyde, petitgrain oil, hexylcinnamaldehyde, cis-3-hexenol, Peru balsam, vetiver oil, vetiverol, peppermint oil, pepper oil, heliotropin, bergamot oil, benzyl benzoate, borneol, mil resinoid, musk ketone, methylnonylacetaldehyde, γ-methylionone, menthol, L-menthol, L-menthone, *Eucalyptus globulus* oil, β-ionone, lime oil, lavender oil, D-limonene, linalool, lyral, filial, lemon oil, rose absolute, rose oxide, rose oil, rosemary oil, and various essential oils, and various perfume blends of the synthetic perfumes and the natural perfumes.

Preferred examples of the coloring agent, the colorant, the dye, and the pigment include legal colors, such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green. No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes, such as Acid Red 14; basic dyes, such as Arianor Sienna Brown, Arianor Madder Red, Arianor Steel Blue, and Arianor Straw Yellow; nitro dyes, such as HC Yellow 2, HC Yellow 5, HC Red 3,4-hydroxypropylamino-3-nitrophenol, N,N'-bis(2-hydroxyethyl)-2-nitro-p-phenylenediamine, HC Blue 2, and Basic Blue 26; disperse dyes; inorganic white pigments, such as titanium dioxide and zinc oxide; inorganic red pigments, such as iron oxide (red iron oxide) and iron titanate; inorganic brown pigments, such as γ-iron oxide; inorganic yellow pigments, such as yellow iron oxide and ocher; inorganic black pigments, such as black iron oxide and low-order titanium oxide; inorganic violet pigments, such as mango violet and cobalt violet; inorganic green pigments, such as chromium oxide, chromium hydroxide, and cobalt titanate; inorganic blue pigments, such as ultramarine and prussian blue; pearl pigments, such as titanium oxide-coated mica, titanium oxide-coated bismuth oxychloride, titanium oxide-coated talc, colored titanium oxide-coated mica, bismuth oxychloride, and fish scale; metal powder pigments, such as aluminum powder, copper powder, and gold; surface treated inorganic and metal powder pigments; organic pigments, such as zirconium lake, barium lake, and aluminum lake; surface treated organic pigments; natural coloring agents and dyes, such as anthraquinones such as astaxanthin and alizarin, naphthoquinones such as anthocyanidin, β-carotene, catenal, capsanthin, chalcone, carthamin, quercetin, crocin, chlorophyll, curcumin, cochineal, and shikonin, bixin, flavones, betacyanidine, henna, hemoglobin, lycopene, riboflavin, and rutin; oxidation dye intermediates and couplers, such as p-phenylenediamine, toluene-2,5-diamine, o-, m-, and p-aminophenols, m-phenylenediamine, 5-amino-2-methylphenol, resorcin, 1-naphthol, and 2,6-diaminopyridine, and salts thereof; autoxidizable dyes, such as indoline; and dihydroxyacetone.

Preferred examples of the antiphlogistics and the anti-inflammatory agent include glycyrrhizic acid and derivatives thereof, glycyrrhetic acid derivatives, salicylic acid derivatives, hinokitiol, guaiazulene, allantoin, indomethacin, ketoprofen, ibuprofen, diclofenac, loxoprofen, celecoxib, infliximab, etanercept, zinc oxide, hydrocortisone acetate, prednisone, diphenhydramine hydrochloride, and chlorpheniramine maleate; and plant extracts, such as peach leaf extract and *Artemisia princeps* leaf extract.

Preferred examples of the anti-asthmatic agent, the therapeutic agent for chronic obstructive pulmonary disease, the antiallergic agent, and the immunomodulator include aminophylline, theophyllines, steroids (such as fluticasone and beclomethasone), leukotriene antagonists, thromboxane inhibitors, Intal, β2 agonists (such as formoterol, salmeterol, albuterol, tulobuterol, clenbuterol, and epinephrine), tiotropium, ipratropium, dextromethorphan, dimemorfan, bromhexine, tranilast, ketotifen, azelastine, cetirizine, chlorpheniramine, mequitazine, tacrolimus, ciclosporin, sirolimus, methotrexate, cytokine modulators, interferon, omalizumab, and proteins/antibody pharmaceuticals.

In addition to these ingredients, the solid base material for skin external application and the aqueous composition of the present invention may contain known cosmetic ingredients, known pharmaceutical ingredients, and known food ingredients, such as ingredients described in Japanese Standards of Cosmetic Ingredients, Japanese Cosmetic Ingredients Codex, List of Cosmetics Ingredients Japanese Labelling Names, issued by Japan Cosmetic Industry Association, INCI dictionary (The International Cosmetic Ingredient Dictionary and Handbook), Japanese Standards of Quasi-drag Ingredients, Japanese Pharmacopoeia, Japanese Pharmaceutical Excipients, Japan's Specifications and Standards for Food Additives, and other standards, and ingredients described in Japanese and foreign patent publications and patent application publications (including Japanese Translations of PCT International applications and Domestic Re-Publications of PCT International applications) categorized as International Patent Classification IPC of A61K7 and A61K8, in a known combination and in a known formulation ratio/formulation amount.

[Method for Producing the Solid Base Material for Skin External Application]

The above-mentioned solid base material for skin external application may be produced in such a manner that a lipid peptide compound including at least one of compounds of the above-mentioned formulae (1) to (3) or pharmaceutically usable salts thereof is mixed with a surfactant and water, and furthermore, if desired, with other ingredients, and stirred while being heated, and then, the mixture is left standing to cool.

EXAMPLES

Hereinafter, the present invention will be more specifically described with reference to Examples, but the present invention is not limited to the following Examples.

Abbreviations used in Examples mean as follows.
Gly: glycine
His: histidine

Apparatuses and conditions used for analysis of physical properties of samples in Examples are listed below.

(pH Measurement)

The pH of a solution that forms a solid base material for skin external application in each Example was measured using Twin pH B-212 (manufactured by Horiba, Ltd.) at room temperature (approximately 25° C.). Note that the pH of the solution that forms a solid base material for skin external application was taken as the pH of the solid base material for skin external application.

(Breaking Strength Measurement Method)

The breaking strength of a solid base material for skin external application was measured using YAMADEN RHEONER II CREEP METER RE2-33005B (manufactured by Yamaden Co., Ltd.) under the conditions of a measurement speed: 0.5 mm/second, a measurement distortion factor: 20%, a storing pitch: 0.10 second, and a jig: 30349-3.

Synthesis Example: Synthesis of Lipid Peptide (N-Palmitoyl-Gly-his)

A lipid peptide used as a gelator in Examples was synthesized in accordance with a method described below.

Into a 4-necked 500-mL flask, 14.2 g (91.6 mmol) of histidine, 30.0 g (91.6 mmol) of N-palmitoyl-Gly-methyl, and 300 g of toluene were charged, and 35.3 g (183.2 mmol) of a sodium methoxide 28% methanol solution was added thereto as a base. The mixture was heated to 60° C. in an oil bath, and stirred for 1 hour. Then, the oil bath was removed, and the solution was allowed to cool to 25° C. To the solution, 600 g of acetone was added to perform reprecipitation, and the resulting solid was collected by filtration. The solid obtained here was dissolved in a mixed solution of 600 g of water and 750 g of methanol. To the solution, 30.5 mL (183.2 mmol) of 6N hydrochloric acid was added to neutralize the solution and precipitate a solid, and the solid was collected by filtration. Next, the obtained solid was dissolved in a mixed solution of 120 g of tetrahydrofuran and 30 g of water at 60° C., and 150 g of ethyl acetate was added thereto. The mixture was cooled from 60° C. to 30° C. Then, the precipitated solid was collected by filtration. Furthermore, the obtained solid was dissolved in a mixed solvent of 120 g of tetrahydrofuran and 60 g of acetonitrile. The solution was heated to 60° C., stirred for 1 hour, and then cooled, followed by filtration. The obtained solid was washed with 120 g of water, collected by filtration, and then was dried under reduced pressure to yield 26.9 g of white crystals of the free form of N-palmitoyl-Gly-His (hereinafter, also simply referred to as Pal-GH) (yield 65%).

Example 1

Into a sample bottle, 5 g of Pal-GH, 2 g of 1,2-hexanediol, 4 g of polyoxyethylene lauryl ether, 0.5 g of stearic acid, and 88.5 g of purified water were charged so as to bring the total amount to 100 g, and the mixture was heated to 80° C. so that all the ingredients were uniformly dissolved. The obtained solution was left standing to cool at room temperature to obtain a solid base material for skin external application.

Next, using the above-mentioned Breaking Strength Measurement Method, the breaking strength of the obtained solid base material for skin external application was measured. FIG. 1 shows the result.

Example 2

Into a sample bottle, the solid base material for skin external application obtained in Example 1 above and water were charged, and heated at 80° C. to be redissolved, and then, 1 mL of a 1 N hydrogen chloride solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 1 shows the result.

Example 3

Into a sample bottle, the solid base material for skin external application obtained in Example 2 above and water were charged, and heated at 80° C. to be redissolved, and then, 1 mL of a 1 N sodium hydroxide solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 1 shows the result.

As shown in FIG. 1, in Example 1, the solid base material for skin external application had a pH in a weak acidic range, and had a sufficient breaking strength value required as a solid base material.

In contrast, in Example 2, the pH of the solid base material for skin external application became acidic, and the breaking strength thereof decreased accordingly, so that a sufficient breaking strength value required as a solid base material was not obtained.

However, in Example 3, in which the pH of the solid base material for skin external application was made weak acidic again by neutralization, the breaking strength of the solid base material for skin external application was recovered, so that the breaking strength reached a sufficient value required as a solid base material.

Example 4

Into a sample bottle, 5 g of Pal-GH, 2 g of 1,2-hexanediol, 4 g of polyoxyethylene lauryl ether, 0.5 g of stearic acid, and 88.5 g of purified water were charged so as to bring the total amount to 100 g, and the mixture was heated to 80° C. so that all the ingredients were uniformly dissolved. The obtained solution was left standing to cool at room temperature to obtain a solid base material for skin external application. Note that the ingredients of the solid base material for skin external application of Example 4 are the very same as those of the solid base material for skin external application of Example 1 above.

Figure 2:
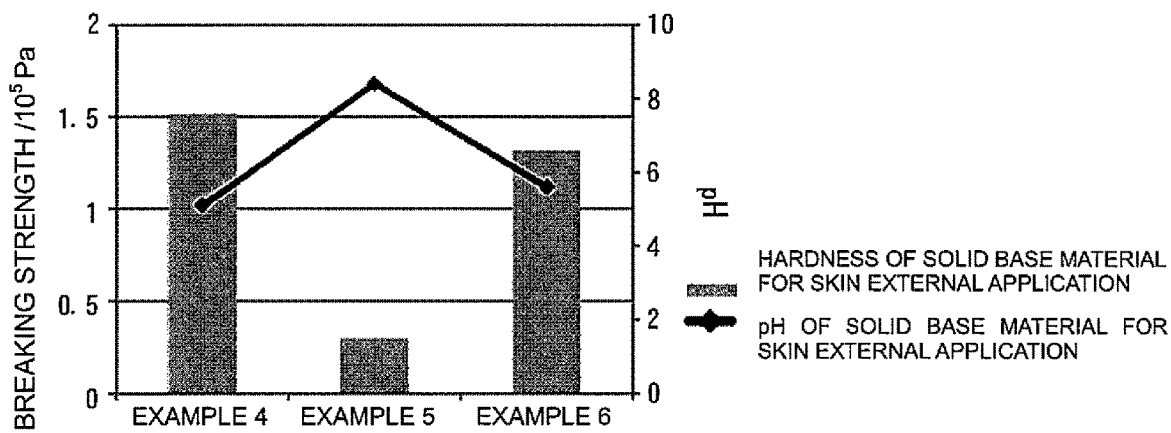
FIG. 2 is a graph showing the measurement results of the breaking strength of solid base materials for skin external application in Examples 4 to 6.

Next, using the above-mentioned Breaking Strength Measurement Method, the breaking strength of the obtained solid base material for skin external application was measured. FIG. 2 shows the result.

Example 5

Into a sample bottle, the solid base material for skin external application obtained in Example 4 above and water were charged, and heated at 80° C. to be redissolved, and then, 1 mL of a 1 N sodium hydroxide solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 2 shows the result.

Example 6

Into a sample bottle, the solid base material for skin external application obtained in Example 5 above and water were charged, and heated at 80° C. to be redissolved, and then, 1 mL of a 1 N hydrogen chloride solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 2 shows the result.

As shown in FIG. 2, in Example 4, the solid base material for skin external application had a pH in a weak acidic range, and had a sufficient breaking strength value required as a solid base material.

In contrast, in Example 5, the pH of the solid base material for skin external application became basic, and the breaking strength thereof decreased accordingly, so that a sufficient breaking strength value required as a solid base material was not obtained.

However, in Example 6, in which the pH of the solid base material for skin external application was made weak acidic again by neutralization, the breaking strength of the solid base material for skin external application was recovered, so that the breaking strength reached a sufficient value required as a solid base material.

Example 7

Into a sample bottle, 5 g of Pal-GH, 2 g of 2-ethyl-1,3-hexanediol, 4 g of polyoxyethylene lauryl ether, 0.25 g of stearic acid, and 88.75 g of purified water were charged so as to bring the total amount to 100 g; and the mixture was heated to 80° C., so that all the ingredients were uniformly dissolved. The obtained solution was left standing to cool at room temperature to obtain a solid base material for skin external application.

Figure 3:
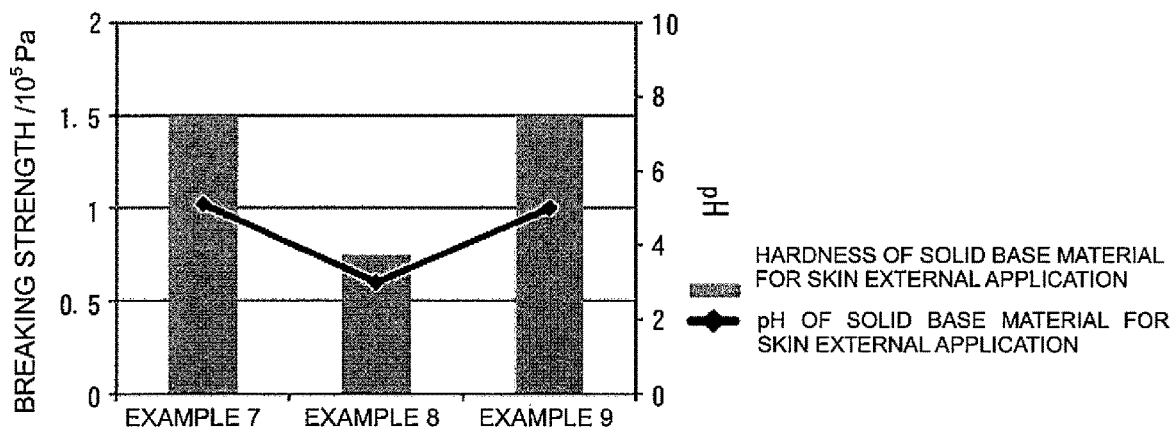
FIG. 3 is a graph showing the measurement results of the breaking strength of solid base materials for skin external application in Examples 7 to 9.

Next, using the above-mentioned Breaking Strength Measurement Method, the breaking strength of the obtained solid base material for skin external application was measured. FIG. 3 shows the result.

Example 8

Into a sample bottle, the solid base material for skin external application obtained in Example 7 above, and water were charged, and heated at 80° C. to be redissolved, and then, 1 mL of a 1 N hydrogen chloride solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 3 shows the result.

Example 9

Into a sample bottle, the solid base material for skin external application obtained in Example 8 above and water were charged, and heated at 80° C. to be redissolved, and then, 1 mL of a 1 N sodium hydroxide solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 3 shows the result.

As shown in FIG. 3, in Example 7, the solid base material for skin external application had a pH in a weak acidic range, and had a sufficient breaking strength value required as a solid base material.

In contrast, in Example 8, the pH of the solid base material for skin external application became acidic, and the breaking strength thereof decreased accordingly, so that a sufficient breaking strength value required as a solid base material was not obtained.

However, in Example 9, in which the pH of the solid base material for skin external application was made weak acidic again by neutralization, the breaking strength of the solid base material for skin external application was recovered, so that the breaking strength reached a sufficient value required as a solid base material.

Example 10

Into a sample bottle, 5 g of Pal-GH, 2 g of 2-ethyl-1,3-hexanediol, 4 g of polyoxyethylene lauryl ether, 0.25 g of stearic acid, and 88.75 g of purified water were charged so as to bring the total amount to 100 g, and the mixture was heated to 80° C. so that all the ingredients were uniformly dissolved. The obtained solution was left standing to cool at room temperature to obtain a solid base material for skin external application. Note that the ingredients of the solid base material for skin external application of Example 10 are the very same as those of the solid base material for skin external application of Example 7 above.

Figure 4:
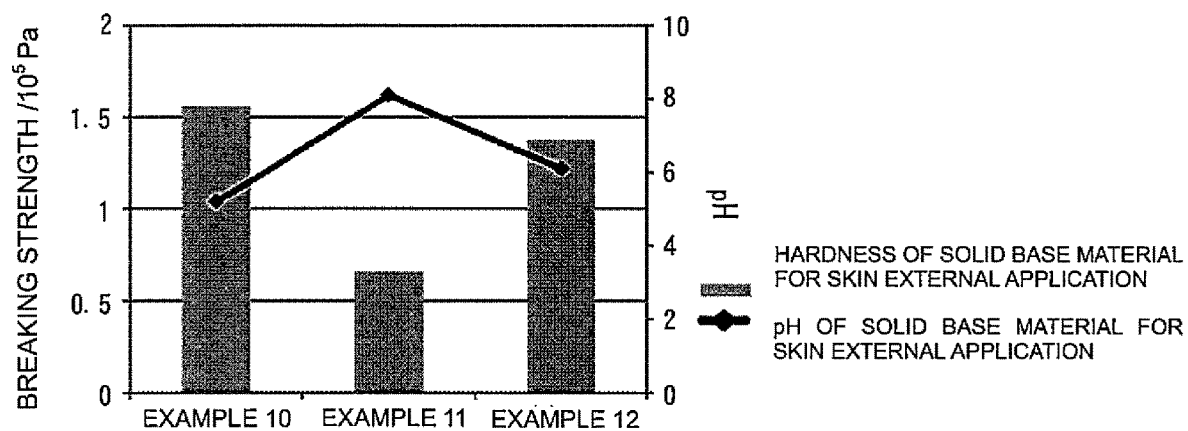
FIG. 4 is a graph showing the measurement results of the breaking strength of solid base materials for skin external application in Examples 10 to 12.

Next, using the above-mentioned Breaking Strength Measurement Method, the breaking strength of the obtained solid base material for skin external application was measured. FIG. 4 shows the result.

Example 11

Into a sample bottle, the solid base material for skin external application obtained in Example 10 above and water were charged, and heated at 80° C. to be redissolved, and then, 1 mL of a 1 N sodium hydroxide solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 4 shows the result.

Example 12

Into a sample bottle, the solid base material for skin external application obtained in Example 11 above, and water were charged, and heated at 80° C. to be redissolved, and then, 1 mL of a 1 N hydrogen chloride solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 4 shows the result.

As shown in FIG. 4, in Example 10, the solid base material for skin external application had a pH in a weak acidic range, and had a sufficient breaking strength value required as a solid base material.

In contrast, in Example 11, the pH of the solid base material for skin external application became basic, and the breaking strength thereof decreased accordingly, so that a sufficient breaking strength value required as a solid base material was not obtained.

However, in Example 12, in which the pH of the solid base material for skin external application was made weak acidic again by neutralization, the breaking strength of the solid base material for skin external application was recovered, so that the breaking strength reached a sufficient value required as a solid base material.

Example 13

At 80° C. 25 g of a composition as Phase A shown in Table 1 below was heated so that all the ingredients thereof were uniformly dissolved. To the resultant solution, 1 g of cetanol as Phase B was added with the temperature maintained at 80° C., so that the mixture was dissolved. Subsequently, to the resultant solution in which Phase A and Phase B were dissolved, Phase C which was beforehand heated to 80° C. was added little by little for dilution so as to bring the total amount of the solution to 100 g, and the resultant diluted solution was stirred to be made uniform. Into a screw tube No. 7 (manufactured by Maruemu Corporation), 40 g of the obtained solution was charged, and left standing to cool at room temperature with being covered with a lid, so that a stick-shaped solid base material for skin external application was obtained.

Figure 5:
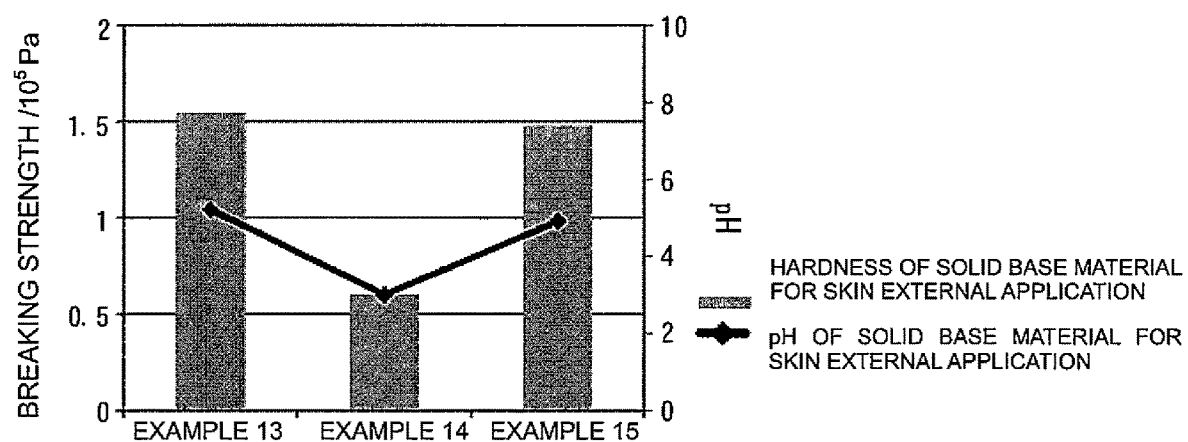
FIG. 5 is a graph showing the measurement results of the breaking strength of solid base materials for skin external application in Examples 13 to 15.

The breaking strength of the obtained solid base material for skin external application was measured in the same manner as the above-mentioned Breaking Strength Measurement Method. FIG. 5 shows the result.

TABLE 1

| Phase A | % by mass (wt %) |
| --- | --- |
| Pal-GH | 20 |
| polyoxyethylene lauryl ether | 16 |
| 2-ethyl-1,3-hexanediol | 8 |
| propylene glycol | 20 |
| stearic acid | 1 |
| purified water | 35 |
| Total | 100 |

TABLE 2

| | Composition | Blending amount (g) |
| --- | --- | --- |
| | Phase A | 25 |
| Phase B | Cetanol | 1 |
| Phase C | purified water | 74 |
| | Total | 100 |

Example 14

Into a sample bottle, the solid base material for skin external application obtained in Example 13 above and water were charged, and heated at 80° C. to be redissolved, and then, 1 mL of a 1 N hydrogen chloride solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 5 shows the result.

Example 15

Into a sample bottle, the solid base material for skin external application obtained in Example 14 above and water were charged, and heated at 80° C. to be redissolved, and then, 1 mL of a 1 N sodium hydroxide solution was added thereto, and the resultant mixture was made uniform. Subsequently, the mixture was left standing to cool at room temperature to obtain a solid base material for skin external application.

The breaking strength of the obtained solid base material for skin external application was measured in the same manner as the above-mentioned Breaking Strength Measurement Method. FIG. 5 shows the result.

As shown in FIG. 5, in Example 13, the solid base material for skin external application had a pH in a weak acidic range, and had a sufficient breaking strength value required as a solid base material.

In contrast, in Example 14, the pH of the solid base material for skin external application became acidic, and the breaking strength thereof decreased accordingly, so that a sufficient breaking strength value required as a solid base material was not obtained.

However, in Example 15, in which the pH of the solid base material for skin external application was made weak acidic again by neutralization, the breaking strength of the solid base material for skin external application was recovered, so that the breaking strength reached a sufficient value required as a solid base material.

The invention claimed is:

1. A method for adjusting hardness of a gelled solid base material for skin external application, the solid base material including a surfactant, water, and a lipid peptide compound including at least one of compounds of formulae (1) to (3) or pharmaceutically usable salts of the compounds represented by:

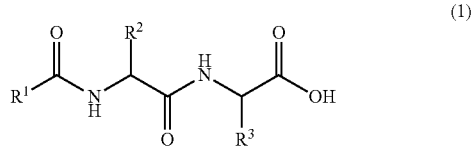
(1)

wherein $R^1$ is a $C_{9-23}$ aliphatic group; $R^2$ is a hydrogen atom, or a $C_{1-4}$ alkyl group that optionally has a $C_1$ or $C_2$ branched chain; and $R^3$ is a —$(CH_2)_n$—X group, n is a number from 1 to 4, and X is amino group, guanidino group, —$CONH_2$ group, or a 5-membered or 6-membered ring group that optionally has 1 to 3 nitrogen atoms, or a condensed heterocycle group composed of the 5-membered ring and the 6-membered ring,

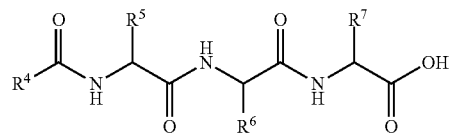
(2)

wherein $R^4$ is a $C_9$-23 aliphatic group; $R^5$ to $R^7$ are each independently a hydrogen atom, a $C_{1-4}$ alkyl group that optionally has a $C_1$ or $C_2$ branched chain, or a —$(CH_2)_n$—X group, n is a number from 1 to 4, and X is amino group, guanidino group, —$CONH_2$ group, or a 5-membered or 6-membered ring group that optionally has 1 to 3 nitrogen atoms, or a condensed heterocycle group composed of the 5-membered ring and the 6-membered ring, and

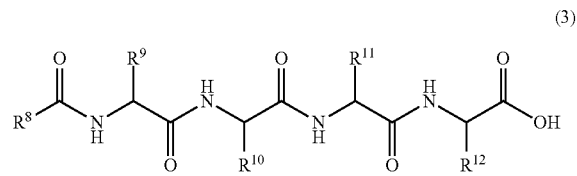
(3)

wherein $R^8$ is a $C_{9-23}$ aliphatic group; $R^9$ to $R^{12}$ are each independently a hydrogen atom, a $C_{1-4}$ alkyl group that optionally has a $C_1$ or $C_2$ branched chain, or a —$(CH_2)_n$—X group, n is a number from 1 to 4, and X is amino group, guanidino group, —$CONH_2$ group, or a 5-membered or 6-membered ring group that optionally has 1 to 3 nitrogen atoms, or a condensed heterocycle group composed of the 5-membered ring and the 6-membered ring, the method comprising:

forming a solution by dissolving the solid base material for skin external application, in stick-shaped form, in water or other solvent;

adding a pH adjuster to the solution in which the solid base material for skin external application is dissolved, to adjust the pH of the solution to a weak acidic to neutral range; and subsequently, forming the solution to re-form a solid base material for skin external application.

2. The method according to claim 1, wherein the solution adjusted to be in the weak acidic to neutral range has a pH of 3.0 to 7.5.

3. The method according to claim 1, wherein the pH adjuster is acetic acid, hydrochloric acid, sulfuric acid, sodium hydroxide, potassium hydroxide, or aqueous ammonia.

4. The method according to claim 1, wherein the solid base material for skin external application is used for cosmetics or pharmaceuticals.

5. The method according to claim 1, wherein the re-formed solid base material for skin external application is stick-shaped.

* * * * *